United States Patent [19]
Myers et al.

[11] Patent Number: 6,159,978
[45] Date of Patent: Dec. 12, 2000

[54] QUINOLINE AND QUINOXALINE COMPOUNDS WHICH INHIBIT PLATELET-DERIVED GROWTH FACTOR AND/OR P56$^{LCK}$ TYROSINE KINASES

[75] Inventors: Michael R. Myers, Reading; Alfred P. Spada, Lansdale, both of Pa.; Paul E. Persons, Westborough; Martin P. Maguire, Woburn, both of Mass.

[73] Assignee: Aventis Pharmaceuticals Product, Inc., Bridgewater, N.J.

[21] Appl. No.: 09/198,716

[22] Filed: Nov. 24, 1998

Related U.S. Application Data

[63] Continuation-in-part of application No. PCT/US98/10999, May 28, 1998, which is a continuation-in-part of application No. 08/972,614, Nov. 18, 1997, abandoned, which is a continuation-in-part of application No. 08/864,455, May 28, 1997, abandoned.

[51] Int. Cl.$^7$ .................. A61K 31/498; C07D 241/36
[52] U.S. Cl. ................. 514/252.1; 514/255.06; 544/353; 544/354; 544/356; 544/344
[58] Field of Search .............. 514/249, 252.1, 514/255.06; 544/353, 354, 356, 346

[56] References Cited

U.S. PATENT DOCUMENTS

| | | | |
|---|---|---|---|
| 3,272,824 | 9/1966 | Ebetino et al. | 514/311 |
| 4,661,499 | 4/1987 | Young et al. | 514/311 |
| 5,336,518 | 8/1994 | Narayanan et al. | 623/1 |
| 5,409,930 | 4/1995 | Spada et al. | 514/248 |
| 5,480,883 | 1/1996 | Spada et al. | 514/249 |
| 5,605,696 | 2/1997 | Eury et al. | 424/423 |
| 5,637,113 | 6/1997 | Tartaglia et al. | 623/1 |
| 5,646,153 | 7/1997 | Spada et al. | 514/259 |
| 5,650,514 | 7/1997 | Stoltefuss et al. | 546/153 |
| 5,700,286 | 12/1997 | Tartaglia et al. | 623/1 |
| 5,700,823 | 12/1997 | Hirth et al. | 514/380 |
| 5,760,066 | 6/1998 | Tang | 514/378 |
| 5,824,049 | 10/1998 | Ragheb et al. | 623/1 |

FOREIGN PATENT DOCUMENTS

| | | |
|---|---|---|
| 0 026 622 | 4/1981 | European Pat. Off. . |
| 0 065 287 | 11/1982 | European Pat. Off. . |
| 0293071 | 11/1988 | European Pat. Off. . |
| WO 92/20642 | 11/1992 | WIPO . |
| WO 95/19169 | 7/1995 | WIPO . |
| WO 95/21613 | 8/1995 | WIPO . |
| WO 95/24190 | 9/1995 | WIPO . |
| WO 98/54157 | 12/1998 | WIPO . |
| WO 98/54158 | 12/1998 | WIPO . |

OTHER PUBLICATIONS

Maguire et al., A New Series of PDGF Receptor Tyrosine Kinase Inhibitors: 3–Substituted Quinoline Derivatives, J. Med. Chem., 1994, 37, 2129–2137.

Preparation of 3–(N–aryl–and N–heterocyclaminomethyl)indole derivatives having excellent efffect . . . nerve growth factor, Chem. Abstracts, vol. 125, No. 15, p. 1213, col. 2, No. 195667C.

Rice et al., Specific Inhibitors of Platelet–Derived Growth Factor or Epidermal Growth Factor Receptor Tyrosine Kinase Reduce Pulmonary Fibrosis in Rats, Am. J. Pathol., 1999, 155(a), pp. 213–221.

Heldin et al., Mechanism of Action and In Vivo Role of Platelet–Derived Growth Factor, Physiological Reviews, 1999, 79(4), pp. 1283–1316.

Loriga et al., Quinoxaline Chemistry. Part 4. 2–(R)–Anilinoquinoxalines as Nonclassical Antifolate Agents., II Famaco, 50 (5), 289–301 (1995).

Kim et al., A Selective Synthesis of Isoxazolo [2,3–1] quinoxalines and Pyrrolo[1,2–a]quinoxalines by 1, 3–Dipolar Cycloaddition Reaction, Journal of the Korean Chemical Society, vol. 34, No. 5, 1990, pp. 469–475. Abstract.

Rewcastle et al., Tyrosine Kinase Inhibitors, J. Med. Chem. 1995, 38, 3482–3487.

Newbold et al., The Oxidation of 2–Hydroxyquinoxaline and its Derivatives with Hydrogen Peroxide, J. Chem Soc., 1948 (519–522).

Makino et al., The Syntheses of Novel 2–(2–Quinoxalinyl) Pyridazine–3(2H)–Ones, Heterocycles, vol. 23, No. 10, 1985, pp. 2603–2611.

Burke, Jr., Protein–Tyrosine Kinases: Potential Targets for Anticancer Drug Development, Stem Cells, 1994: 12:1–6.

N–Quinoxalinylanilines, Chemical Abstracts, vol. 103, 1985, 160539f.

Lin et al., Studies on antiarrhythmics, Chemical Abstracts, vol. 96, 1982, 122728w.

Takase et al., Preparation of N–containing heterocyclic compounds as phosphodiesterase inhibitors, Chemical Abstracts, vol. 119, 1993, 203427t.

Hirth et al., , Derwent computer search, 1995, 861279.

Derwent Information Ltd., 1982–64774E JP57102871 Abstract.

Derwent Information Ltd., 1985–168512 Abstract.

Shawyer et al., Inhibition of Platelet–derived Growth Factor–mediated Signal Transduction and Tumor Growth by N–[4–(Trifluoromethyl10–phenyl] 5–Methylisoxazole–4–carboxamide, Clinical Cancer Research, vol. 3, 1167–1177, Jul. 1997.

Klutchko et al., 2–Substituted Aminopyrido[2,3–d] pyrimidin-7(8H)–ones., J. Med. Chem., 1998, 41, 3276–3292.

Sakata et al., , Chem. Abstract, Nippon Noyaku Gakkasishi, 19(1), 61–7, (1985); 109577.

Zellner et al. "Synth.v.Chino.–Derv.";Helv.Chim.Acta49/2, 913(1966)/CA64:15882d, Feb. 1966.

Zellner et al, Chemical Abstracts, vol. 64,#15882, Feb. 1966.

*Primary Examiner*—Mukund J. Shah
*Assistant Examiner*—Sudhaker B. Patel
*Attorney, Agent, or Firm*—Irving Newman; Peter Butch

[57] ABSTRACT

This invention is directed to quinoline/quinoxaline compounds which inhibit platelet-derived growth factor tyrosine kinase and/or Lck tyrosine kinase, to pharmaceutical compositions comprising these compounds, and to the use of these compounds for treating a patient suffering from or subject to disorders/conditions involving cellular differentiation, proliferation, extracellular matrix production or mediator release and/or T cell activation and proliferation.

36 Claims, No Drawings

QUINOLINE AND QUINOXALINE COMPOUNDS WHICH INHIBIT PLATELET-DERIVED GROWTH FACTOR AND/OR P56$^{LCK}$ TYROSINE KINASES

CROSS REFERENCE TO RELATED APPLICATIONS

This is a continuation-in-part of International Patent Application No. PCT/US98/10999, filed May 28, 1998, which in turn is a continuation-in-part of U.S. Ser. No. 08/972,614, filed Nov. 18, 1997, now abandoned which in turn is a continuation-in-part of U.S. Ser. No. 08/864,455, filed May 28, 1997, now abandoned.

BACKGROUND OF THE INVENTION

1. Field of the Invention

This invention is directed to the inhibition of cell proliferation and/or cell matrix production and/or cell movement (chemotaxis) and/or T cell activation and proliferation using of quinoline/quinoxaline compounds which are useful protein tyrosine kinase inhibitors (TKIs).

Cellular signaling is mediated through a system of interactions which include cell—cell contact or cell-matrix contact or extracellular receptor-substrate contact. The extracellular signal is often communicated to other parts of the cell via a tyrosine kinase mediated phosphorylation event which affects substrate proteins downstream of the cell membrane bound signaling complex. A specific set of receptor-enzymes such as the insulin receptor, epidermal growth factor receptor (EGF-R) or platelet-derived growth factor receptor (PDGF-R) are examples of tyrosine kinase enzymes which are involved in cellular signaling. Autophosphorylation of the enzyme is required for efficient enzyme-mediated phosphorylation of substrate proteins containing tyrosine residues. These substrates are known to be responsible for a variety of cellular events including cellular proliferation, cellular matrix production, cellular migration and apoptosis to name a few.

It is understood that a large number of disease states are caused by either uncontrolled reproduction of cells or overproduction of matrix or poorly regulated programmed cell death (apoptosis). These disease states involve a variety of cell types and include disorders such as leukemia, cancer, glioblastoma, psoriasis, inflammatory diseases, bone disease, fibrotic diseases, artherosclerosis and restenosis occurring subsequent to angioplasty of the coronary, femoral or kidney arteries or, fibroproliferative disease such as in arthritis, fibrosis of the lung, kidney and liver. In addition, deregulated cellular proliferative conditions follow from coronary bypass surgery. The inhibition of tyrosine kinase activity is believed to have utility in the control of uncontrolled reproduction of cells or overproduction of matrix or poorly regulated programmed cell death (apoptosis).

It is also known that certain tyrosine kinase inhibitors can interact with more than one type of tyrosine kinase enzyme. Several tyrosine kinase enzymes are critical for the normal function of the body. For instance, it would be undesirable to inhibit insulin action in most normal circumstances. Therefore, compounds which inhibit PDGF-R tyrosine kinase activity at concentrations less than the concentrations effective in inhibiting the insulin receptor kinase could provide valuable agents for the selective treatment of disease characterized by cell proliferation and/or cell matrix production and/or cell movement (chemotaxis) such as restenosis.

This invention relates to the modulation and/or inhibition of cell signaling, cell proliferation, extracellular matrix production, chemotaxis, the control of abnormal cell growth and cell inflammatory response. More specifically, this invention relates to the use of substituted quinoxaline compounds which exhibit selective inhibition of differentiation, proliferation or mediator release by effectively inhibiting platelet-derived growth factor-receptor (PDGF-R) tyrosine kinase activity and/or Lck tyrosine kinase activity.

2. Reported Developments

A number of literature reports describe tyrosine kinase inhibitors which are selective for tyrosine kinase receptor enzymes such as EGF-R or PDGF-R or non-receptor cytosolic tyrosine kinase enzymes such as v-abl, p56lck or c-src. Recent reviews by Spada and Myers (*Exp. Opin. Ther. Patents* 1995, 5(8), 805) and Bridges (*Exp. Opin. Ther. Patents* 1995, 5(12), (1245) summarize the literature for tyrosine kinase inhibitors and EGF-R selective inhibitors respectively. Additionally, Law and Lydon have summarized the anticancer potential of tyrosine kinase inhibitors (*Emerging Drugs: The Prospect For Improved Medicines* 1996, 241–260).

Known inhibitors of PDGF-R tyrosine kinase activity includes quinoline-based inhibitors reported by Maguire, et al. (*J. Med. Chem.* 1994, 37, 2129), and by Dolle et al. (*J. Med. Chem.* 1994, 37, 2627). A class of phenylaminopyrimidine-based inhibitors was recently reported by Traxler et. al. in EP 564409 and by Zimmerman, J.; and Traxler, P. et al. (*Biorg. & Med. Chem. Lett.* 1996, 6(11), 1221–1226) and by Buchdunger, E. et al. (*Proc. Nat. Acad. Sci.* 1995, 92, 2558). Despite the progress in the field there are no agents from these classes of compounds that have been approved for use in humans for treating proliferative disease.

The correlation between the multifactorial disease of restenosis with PDGF and PDGF-R is well-documented throughout the scientific literature. However, recent developments into the understanding of fibrotic diseases of the lung (Antoniades, H. N.; et al. *J. Clin. Invest.* 1990, 86, 1055), kidney and liver (Peterson, T. C. *Hepatology,* 1993, 17, 486) have also implicated PDGF and PDGF-R as playing a role. For instance glomerulonephritis is a major cause of renal failure and PDGF has been identified to be a potent mitogen for mesangial cells in vitro as demonstrated by Shultz et al. (*Am. J. Physiol.* 1988, 255, F674) and by Floege, et al. (*Clin. Exp. Immun.* 1991, 86, 334). It has been reported by Thornton, S. C.; et al. (*Clin. Exp. Immun.* 1991, 86, 79) that TNF-alpha and PDGF (obtained from human rheumatoid arthritis patients) are the major cytokines involved in proliferation of synovial cells. Furthermore, specific tumor cell types have been identified (see Silver, B, J., *BioFactors,* 1992, 3, 217) such as glioblastoma and Kaposi's sarcoma which overexpress either the PDGF protein or receptor thus leading to the uncontrolled growth of cancer cells via an autocrine or paracrine mechanism. Therefore, it is anticipated that a PDGF tyrosine kinase inhibitor would be useful in treating a variety of seemingly unrelated human disease conditions that can be characterized by the involvement of PDGF and or PDGF-R in their etiology.

The role of various non-receptor tyrosine kinases such as p56$^{lck}$ (hereinafter "Lck") in inflammation-related conditions involving T cell activation and proliferation has been reviewed by Hanke, et al (*Inflamm. Res.* 1995, 44, 357) and by Bolen and Brugge (*Ann. Rev. Immunol.,* 1997, 15, 371). These inflammatory conditions include allergy, autoimmune disease, rheumatoid arthritis and transplant rejection. Another recent review summarizes various classes of tyrosine kinase inhibitors including compounds having Lck inhibitory activity (Groundwater, et. al *Progress in Medicinal Chemistry*, 1996, 33, 233). Inhibitors of Lck tyrosine kinase activity include several natural products which are generally non-selective tyrosine kinase inhibitors such as staurosporine, genistein, certain flavones and erbstatin. Damnacanthol was recently reported to be a low nM inhibitor of Lck (Faltynek, et. al, *Biochemistry*, 1995, 34, 12404). Examples of synthetic Lck inhibitors include: a series of dihydroxy-isoquinoline inhibitors reported as having low micromolar to submicromolar activity (Burke, et. al *J. Med. Chem.* 1993, 36, 425); and a quinoline derivative found to be much less active having an Lck $Ic_{50}$ of 610 micromolar. Researchers have also discloses a series of 4-substituted quinazolines that inhibit Lck in the low micromolar to submicromolar range (Myers et al, WO95/15758 and Myers, et. al *Bioorg. Med. Chem. Lett.* 1977, 7, 417). Researchers at Pfizer (Hanke, et. al *J. Biol. Chem.* 1996, 271, 695) have disclosed two specific pyrazolopyrimidine inhibitors known as PP1 and PP2 which have low nanomolar potency against Lck and Fyn. (another Src-family kinase). No Lck inhibitory has been reported regarding quinoline or quinoxaline based compounds. Therefore, it is anticipated that a quinoline or quinoxaline based inhibitor of Lck tyrosine kinase activity could be useful in treating a variety of seemingly unrelated human disease conditions that can be characterized by the involvement of Lck tyrosine kinase signaling in their etiology.

SUMMARY OF THE INVENTION

This invention is directed to a compound of Formula I:

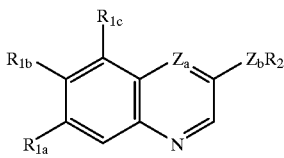

(I)

wherein $R_{1a}$ is optionally substituted alkyl, hydroxy, acyloxy, optionally alkoxy, optionally substituted cycloalkyloxy, optionally substitutes oxaheterocyclyloxy, optionally substituted heteroyclylcarbonyloxy or halo;

$R_{1b}$ is hydrogen, optionally substituted alkyl, hydroxy, acyloxy, optionally substituted alkoxy, optionally substituted cycloalkyloxy, optionally substituted oxaheterocyclyloxy, optionally substituted heterocyclylcarbonyloxy or halo;

$R_{1c}$ is hydrogen, optionally substituted alkyl, optionally substituted aryl, optionally substituted heteroaryl, hydroxy, acyloxy, optionally substituted alkoxy, optionally substituted cycloalkyloxy, optionally substituted heterocycloxy, optionally substituted aryloxy, optionally substituted heteroaryloxy, optionally substituted heterocyclylcarbonyloxy, halo, cyano, $R_5R_6N$— or acyl$R_5N$—;

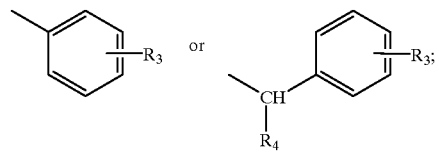

$R_2$ is $R_3$ is hydrogen, or ortho or para fluoro, or meta lower alkyl, lower alkoxy, halo or carbamoyl;

$R_4$ is hydrogen or lower alkyl;

$R_5$ and $R_6$ are independently hydrogen or alkyl, or $R_5$ and $R_6$ taken together with the nitrogen atom to which $R_5$ and $R_6$ are attached form azaheterocyclyl;

$Z_a$ is N or CH; and $Z_b$ is NH or O, or an N-oxide thereof, hydrate thereof, solvate thereof, prodrug thereof, or salt thereof, provided that $R_{1a}$ and $R_{1b}$ are not both optionally substituted alkyl.

Another aspect of the invention is directed to a pharmaceutical composition comprising a pharmaceutically effective amount of a compound of formula I and a pharmaceutically acceptable carrier. The invention is also directed to intermediates useful in preparing compounds of formula I, methods for the preparation of the intermediates and compounds of formula I, and the use of a compound of formula I for treating a patient suffering from or subject to disorders/conditions involving cellular differentiation, proliferation, extracellular matrix production or mediator release.

DETAILED DESCRIPTION OF THE INVENTION

As used above, and throughout the description of the invention, the following terms, unless otherwise indicated, shall be understood to have the following meanings:

Definitions

"Patient" means a mammal including a human.

"Effective amount" means an amount of compound of the present invention effective in inhibiting PDGF-R tyrosine kinase activity and or Lck tyrosine kinase activity, and thus producing the desired therapeutic effect.

"Alkyl" means aliphatic hydrocarbon group which may be branched-or straight-chained having about 1 to about 10 carbon atoms. Preferred alkyl is "loweralky" having about 1 to about 3 carbon atoms; more preferred is methyl. Branched means that one or more lower alkyl groups such as methyl, ethyl or propyl are attached to a linear alkyl chain. The alkyl group is also optionally substituted by alkoxy, halo, carboxy, hydroxy or $R_5R_6N$— (wherein $R_5$ and $R_6$ are independently hydrogen or alkyl, or $R_5$ and $5_6$ taken together with the nitrogen atom to which $R_5$ and $R_6$ are attached form azaheterocyclyl); more preferably optionally substituted by fluoro. Examples of alkyl include methyl, fluoromethyl, difluoromethyl, trifluoromethyl, ethyl, n-propyl, isopropyl, butyl, sec-butyl, t-butyl, amyl and hexyl.

"Cycloalkyl" means a non-aromatic monocyclic ring system of about 3 to about 7 carbon atoms. Preferred monocyclic cycloalkyl rings include cyclopentyl, cyclohexyl and cycloheptyl; more preferred are cyclohexyl and cyclopentyl.

"Aryl" means aromatic carbocyclic radical containing about 6 to about 10 carbon atoms. Exemplary aryl include phenyl or naphthyl, or phenyl or naphthyl substituted with one or more aryl group substituents which may be the same or different, where "aryl group substituent" includes hydrogen, hydroxy, halo, alkyl, alkoxy, carboxy, alkoxycarbonyl or $Y^1Y^2NCO$—, wherein $Y^1$ and $Y^2$ are independently hydrogen or alkyl.

"Heteroaryl" means about a 5- to about a 10- membered aromatic monocyclic or multicyclic hydrocarbon ring system in which one or more of the carbon atoms in the ring system is/are elements(s) other than carbon, for example nitrogen, oxygen or sulfur. The "hetroaryl"may also be substituted by one or more of the above-mentioned "aryl group substituents". Exemplary heteroaryl groups include substituted pyrazinyl, furanyl, thienyl, pyridyl, pyrimidinyl, isoxazolyl, isothiazolyl, oxazolyl, thiazoly, pyrazolyl, furazanyl, pyrrolyl, imidazo[2,1-b]thiazolyl, benzofurzanyl, indolyl, azaindolyl, benzimidazolyl, benzothienyl, quinolinyl, imidazolyl and isoquinolinyl.

"Heterocyclyl" means an about 4 to about 7 member monocyclic ring system wherein one or more of the atoms in the ring system is an element other than carbon chosen amongst nitrogen, oxygen or sulfur. The designation of the aza or oxa as a prefix before heterocyclyl define that at least a nitrogen, or oxygen atom is present respectively as a ring atom. Exemplary monocyclic heterocyclyl groups include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. Exemplary heterocyclyl moieties include quinuclidyl, pentamethylenesulfide, tetrahydropyranyl, tetrahydrothiphenyl, pyrrolidinyl, tetrahydrofuranyl or 4-piperidinipiperidine.

"Heterocyclylcarbonyloxy" means a heterocyclyl-C(O) O— group wherein the heterocyclyl is as defined herein. An exemplary heterocyclylcarbonyloxy group is [1,4']-bipiperidin-1'-ylcarbonyloxy (4-piperidonopiperid-1-ylcarbonyloxy).

"Acyl" means an H—CO— or alkyl-CO— group in which the alkyl group is as previously described. Preferred acyls contain a lower alkyl. Exemplary acyl groups include formyl, acetyl, propanoyl, 2-methylpropanoyl, butanoyl and caproyl.

"Alkoxy" means an alkyl-O— group in which the alkyl group is as previously described. Preferred alkoxy is "lower alkoxy" having about 1 to about 3 carbon atoms; more preferred is methoxy. The alkoxy may be optionally substituted by one or more alkoxy, carboxy, alkoxycarbonyl, carboxyaryl or $R_5R_6N$— (wherein $R_5$ and $R_6$ are as defined above). Exemplary alkoxy groups include methoxy, ethoxy, n-propoxy, i-propoxy, n-butoxy, heptoxy, 2-(morpholin-4-yl)ethoxy and 2-(ethoxy)ethoxy.

"Cycloalkyloxy" means a cycloalkyl-O— group in which the cycloalkyl group is as previously described. Exemplary cycloalkyloxy groups include cyclopentyloxy or cyclohexyloxy.

"Heterocyclyloxy" means a heterocyclyl-O— group in which the heterocyclyl group is previously described. Exemplary heterocyclyloxy groups include pentamethylenesulfideoxy, tetrahydropyranyloxy, tetrahydrothiophenyloxy, pyrrolidinyloxy or tetrahydrofuranyloxy.

"Aryloxy" means aryl-O— group in which the aryl group; is as previously described.

"Heteroaryloxy" means heteroaryl-O— group in which the heteroaryl group is as previously described.

"Acyloxy" means and acyl-O— group in which the acyl group is as previously described.

"Carboxy" means a HO(O)C— (carboxylic acid) group.

"$R_5R_6N$—" means a substituted or unsubstituted amino group, wherein $R_5$ and $R_6$ are as previously described. Exemplary groups include amino ($H_2N$—), methylamino, ethylmethylamino, dimethylamino and diethylamino.

"$R_5R_6NCO$—" means a substituted or unsubstituted carbomoyl group, wherein $R_5$ and $R_6$ are as previously described. Exemplary groups are carbamoyl ($H_2NCO$—) are dimethylaminocarbamoyl ($Me_2NCO$—).

"Acyl$R_5N$—" means an acylamino group wherein $R_5$ and acyl are as defined herein.

"Halo" means fluoro, chloro, bromo, or iodo. Preferred are fluoro, chloro or bromo, and more preferred are fluoro or chloro.

"Prodrug" means a form of the compound of formula I suitable for administration to a patient without undue toxicity, irritation, allergic response, and the like, and effective for their intended use, including ketal, ester and zwitterionic forms. A prodrug is transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A. C. S. Symposium Series, and in Edward B. Roche, et., *Bioreversible Carriers in Drug Design*, American Pharmaceutical Association and Pergamon Press, 1987, both of which are incorporated herein by reference.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecule (s) is/are $H_2O$.

Preferred Embodiments

A preferred compound aspect of the invention is a compound of formula I wherein $R_{1a}$ is optionally substituted lower alkoxy, optionally substituted mono cyclic cyloalkyloxy, optionally substituted heterocyclycarbonyloxy or optionally substituted mono cyclic oxaheterocyclyloxy; more preferably $R_{1a}$ is optionally substituted lower alkoxy or optionally substituted mono cyclic oxaheterocyclyloxy; and still more preferred $R_{1a}$ is methoxy, ethoxy, 2-(ethoxy)ethoxy, 2-(4-morpholinyl)ethoxy or furanyloxy.

Another preferred compound aspect of the invention is a compound of formula I wherein $R_{1b}$ is hydrogen, optionally substituted lower alkoxy, optionally substituted mono cyclic cycloalkyloxy, optionally substituted heterocyclycarbonyloxy or optionally substituted mono cyclic oxaheterocyclyloxy; more preferably $R_{1b}$ is hydrogen or optionally substituted lower alkoxy; and yet more preferred $R_{1b}$ is methoxy or ethoxy.

Another preferred compound aspect of the invention is a compound of formula I wherein $R_{1a}$ and $R_{1b}$ are lower alkoxy; more preferably the lower alkoxy is methoxy or ethoxy.

Another preferred compound aspect of the invention is a compound of formula I wherein $R_{1c}$ is hydrogen or optionally substituted lower alkoxy; more preferably is $R_{1c}$ is hydrogen, methoxy or ethoxy.

Another preferred compound aspect of the invention is a compound of formula I wherein $R_2$ is

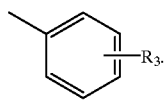

Another preferred compound aspect of the invention is a compound of formula I wherein $R_2$ is

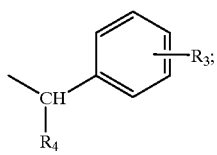

Another preferred compound aspect of the invention is a compound of formula I wherein $R_3$ is hydrogen, ortho or para fluoro, or meta methyl, trifluoromethyl, methoxy, fluoro, chloro, bromo or carbamoyl.

Another preferred compound aspect of the invention is a compound of formula I wherein $R_4$ is hydrogen or methyl;

Another preferred compound aspect of the invention is a compound of formula I wherein $Z_a$ is N.

Another preferred compound aspect of the invention is a compound of formula I wherein $Z_a$ is CH.

Another preferred compound aspect of the invention is a compound of formula I wherein $Z_b$ is NH.

Another preferred compound aspect of the invention is a compound of formula I wherein $Z_b$ is O.

Preferred compounds according to the invention are selected from the following species:

2-anilino-6quinoxalinol;
2-((R)-α-Methylbenzyl-amino)-6,7-diethoxyquinoxaline;
2-anilino-6-isopropoxyquinoxaline;
2-Phenoxy-6-methoxyquinoxaline;
(3-Bromobenzyl)-(6,7-dimethoxyquinoxalin-2-yl)-amine;
2-(3-Carbamoylphenylamino)-6-methoxyquinoxaline;
2-(2-Fluorophenylamino)-6,7-diethoxyquinoxaline;
2-(3-Trifluoromethylphenylamino)-6,7-diethoxyquinoxaline;
Phenyl-[6-(tetrahydrofuran-3(R)-yloxy)quinoxalin-2-yl]amine;
Benzyl-(6,7-dimethoxyquinoxalin-2-yl)-amine;
2-((S)-α-Methylbenzyl-amino)-6,7-diethoxyquinoxaline;
2-Benzylamino-6,7-diethoxyquinoxaline;
(6-Methoxyquinoxalin-2-yl)-(3-methylphenyl)-amine;
6-Methoxy-2-phenylamino-quinoxaline;
2-Anilino-6-ethoxyquinoxaline;
2-(3-Methoxyphenylamino)-6,7-diethoxyquinoxaline;
2-(4-Fluorophenylamino)-6,7-diethoxyquinoxaline;
6,7-Diethoxy-2-phenoxyquinoxaline;
2-Phenylamino-6,7-diethoxyquinoxaline;
(6,7-Dimethoxyquinoxalin-2-yl)-(3-fluorophenyl)-amine;
2-(3-Fluorophenylamino)-6,7-diethoxyquinoxaline;
(3-Bromophenyl)-(6,7-dimethoxyquinoxalin-2-yl)-amine;
(6,7-Dimethoxyquinoxalin-2-yl)-phenyl-amine; and
(3-Chlorophenyl)-(6,7-dimethoxyquinoxalin-2-yl)-amine.

More preferred species are the following:
Phenyl-[6-(tetrahydrofuran-3(R)-yloxy)quinoxalin2-yl]amine;
Benzyl-(6,7-dimethoxyquinoxalin-2-yl)-amine;
2-((S)-α-Methylbenzyl-amino)-6,7-diethoxyquinoxaline;
2-Benzylamino-6,7-diethoxyquinoxaline;
(6-Methoxyquinoxalin-2-yl)-(3-methylphenyl)-amine;
6-Methoxy-2-phenylamino-quinoxaline;
2-Anilino-6-ethoxyquinoxaline;
2-(3-Methoxyphenylamino)-6,7-diethoxyquinoxaline;
2-(4-Fluorophenylamino)-6,7-diethoxyquinoxaline;
6,7-Diethoxy-2-phenoxyquinoxaline;
2-Phenylamino-6,7-diethoxyquinoxaline;
(6,7-Dimethoxyquinoxalin-2-yl)-(3-fluorophenyl)-amine;
2-(3-Fluorophenylamino)-6,7-diethoxyquinoxaline;
(3-Bromophenyl)-(6,7-dimethoxyquinoxalin-2-yl)-amine;
(6,7-Dimethoxyquinoxalin-2-yl)-phenyl-amine; and
(3-Chlorophenyl)-(6,7-dimethoxyquinoxalin-2-yl)-amine.

It is to be understood that this invention covers all appropriate combinations of the particular and preferred groupings referred to herein.

The compounds of this invention may be prepared by employing procedures known in the literature starting from known compounds or readily prepared intermediates. Exemplary general procedures follow.

In addition, compounds of formula I are prepared according to the following Schemes I–VI, wherein the variables are as described above, excepting those variables which one skilled in the art would appreciate would be incongruent with the method described.

Scheme I

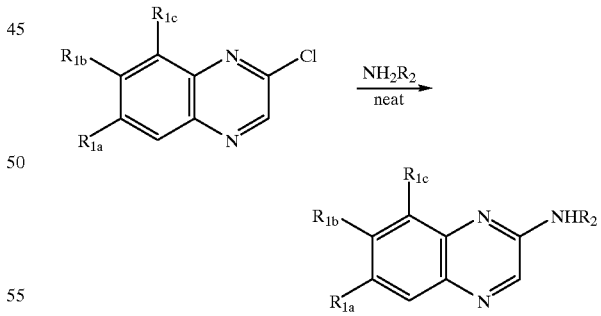

Scheme II

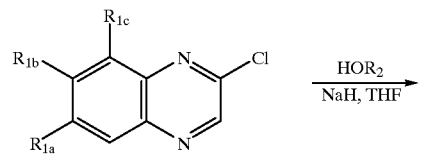

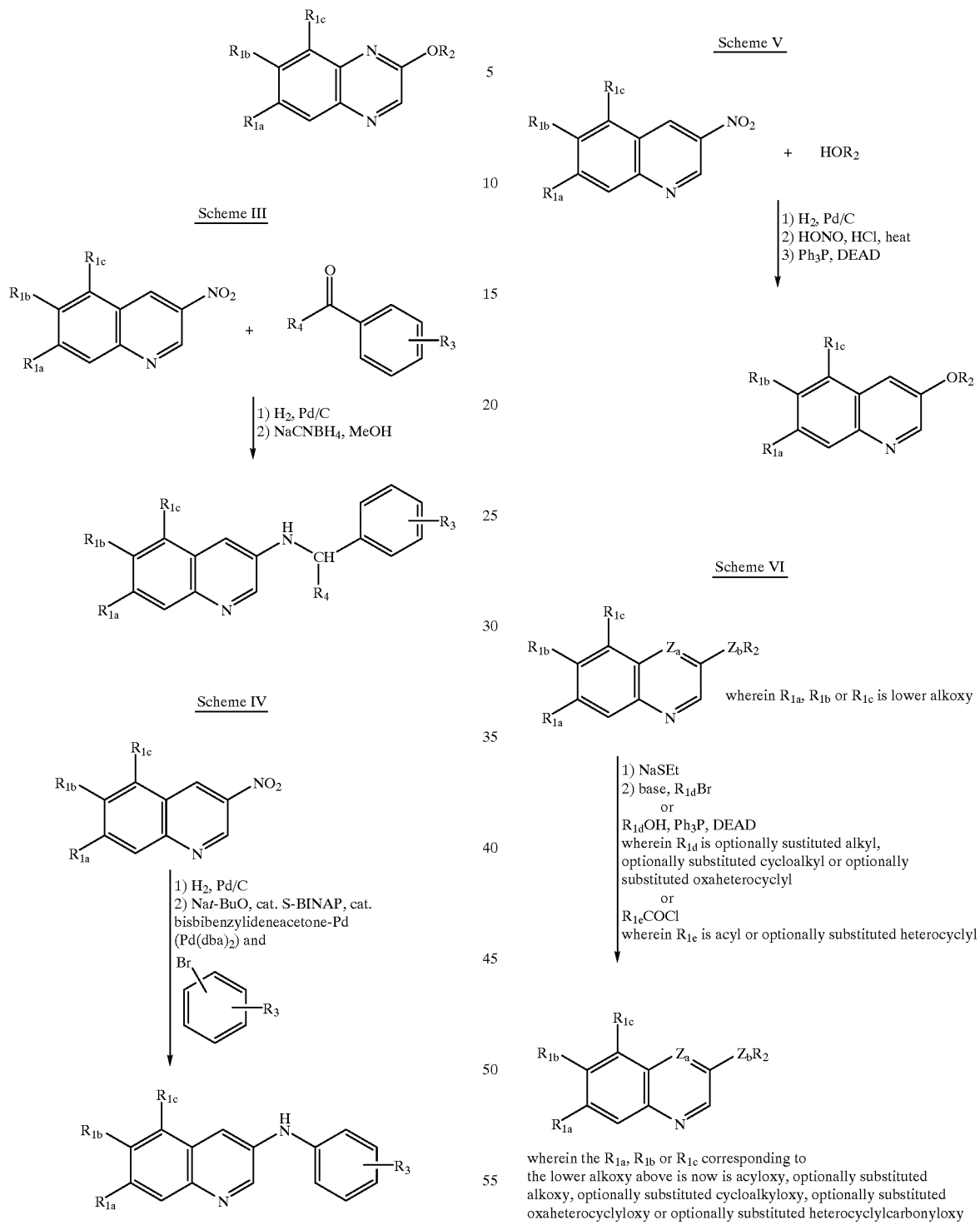

Scheme VII

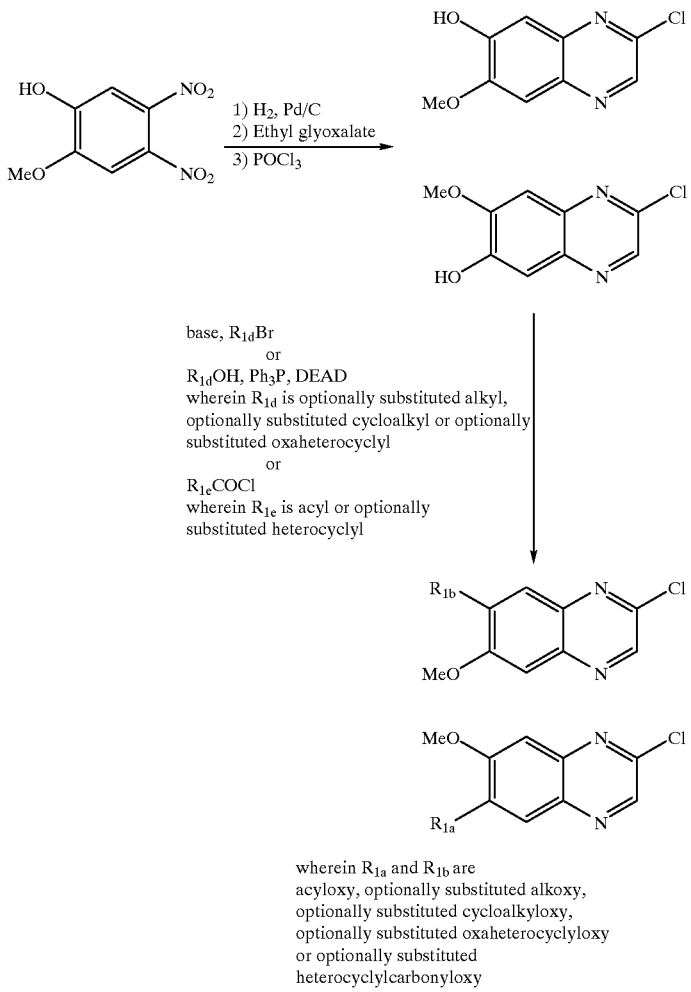

wherein $R_{1a}$ and $R_{1b}$ are
acyloxy, optionally substituted alkoxy,
optionally substituted cycloalkyloxy,
optionally substituted oxaheterocyclyloxy
or optionally substituted
heterocyclylcarbonyloxy

I. General Procedures

1. Coupling of 2-chloro substituted quinoxaline and amines or anilines

A mixture of 2-chloro-6,7-dimethoxyquinoxaline (1 eq.) and an amine (about 1 to about 5 eq.) is heated at about 160 to about 180° C. from about three hours to overnight. The dark-brown residue is dissolved in methanol/methylene chloride (0%–10%) and chromatographed on silica gel eluted with hexane/ethyl or methanol/methylene chloride (0%–100%) to yield the desired product. The desired product may be purified further through recrystallization in methanol, methylene chloride or methanol/water.

2. Coupling of 2-chloro substituted quinoxaline and alcohols or phenols

A suspension of an alcohol or mercaptan (1 eq.) and sodium hydride (about 1 to about 3 eq.) in anhydrous DMF/THF (0%–50%) is refluxed for 1 hour before addition of 2-chloro-6,7-dimethoxyquinoxaline (1 eq.). The resulting mixture is refluxed for about one to about four hours. The suspension is neutralized to about pH5–8 and partitioned between methylene chloride and brine. The residue after concentration of methylene chloride is chromatographed on silica gel eluted with hexane/ethyl acetate or methanol/methylene chloride (0%–100%) to give the desired product.

3. Reductive amination reaction with amino-quinolines and aldehydes or ketones.

An appropriately substituted 3-amino quinoline (1 eq.) is stirred with 1 eq. of the appropriate aldehyde or ketone in methanol (or another suitable solvent mixture) until TLC indicates imine formation is complete. Excess $NaCNBH_4$ or $NaBH_4$, or another suitable reducing agent is added and the mixture is stirred until TLC shows consumption of the intermediate imine. The mixture is concentrated and the residue is chromatographed on silica gel with hexane/ethyl acetate (0–100%) or chloroform/methanol (0–20%) to give the desired product.

4. coupling reaction of 3-amino substituted quinolines and bromophenyl compounds.

An appropriately substituted 3-amino quinoline (1 eq.) is stirred with ~1.4 eq. of a strong base such as sodium t-butoxide, 1 eq. of the appropriate bromophenyl compound, and catalytic amounts of 2,2'-bis(disphenylphosphino)-1-1'-binaphthyl (S-BINAP) and bis(dibenzlideneacetone)-Palladium $(pd(dba)_2)$ are mixed in an inert organic solvent such as tolune under an inert atmosphere such as argon and heated to about 80° C. overnight. The mixture is cooled, diluted with a solvent such as ether, filtered, concentrated and chromatographed with 50% EtOAc/hexane to give the desired product.

5. Ether formation from 3-hydroxy substituted quinolines via Mitsunobu conditions.

A THF solution of an appropriately substituted hydroxyquinoxaline (at about 0 to about 25° C.) is treated with 1 eq. each of the desired alcohol, triphenylphosphine and finally diethlazodicarboxylate (DEAD) or a suitable equivalent. The reaction progress is monitored via TLC and upon completion of the reaction (about 1 to about 24 hours) the mixture is concentrated and the residue is chromatographed on silica gel to yield the desired product.

6. Dealkylation of a lower alkoxy substituted quinoline or quinoxaline, and subsequent alkylation.

An appropriate lower alkoxy substituted quinoline or quinoxaline (1 eq.) in DMF is treated with excess sodium ethanthiolate (usually about 2 or more eq.) and the reaction mixture is stirred with heating from about 1 to about 24 hours. The mixture is partitioned between water and ethyl acetate. Extractive workup followed by chromatography, if necessary, provides the corresponding desired hydroxy substituted quinoline or quinoxaline product.

The hydroxy substituted quinoline or quinoxaline product can be alkylated using the conditions for the Mitsunobu reaction as detailed above. Alternatively, simply alkylation using methods well-known in the art with a relactive alkyl- or benyl-halide using NaH or another appropriate base in a suitable solvent provides the desired alkylated product.

7. Oxidation of a nitrogen in a quinoline or quinoxaline to the corresponding N-oxide.

An imine (=N—) moiety in a quinoline or quinoxaline compound of formula (I), may be converted to the corresponding compound wherein the imine moiety is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts; so that the beneficial inhibitory effects on PDGF inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluensulfonic acid, cyclohexylsulfamic acid, quinic acid, and the like. The corresponding acid addition salts comprise the following: hydrohalides, e.g. hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-$\beta$-hydroxynaphthoates, gentisates, mesylates, isethionates and di-p-toluoyltartrtesmethanesulfonate, ethanesulfonate, benzenesulfonate, p-toluensfulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention can be regenerated from the acid addition salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on PDGF inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, n-methyl-glucamine, lysine, arginine, ornithine, choline, N,N'-dibenzylethylenediamine, chloroprocaine, diethanolamine, procaine, n-benzylphenethylamine, diethylamine, piperazine, tris (hydroxymethyl)-aminomethane, tetramethylammonium hydroxide, and the like.

Metal salts of compounds of the present invention may be obtained by contacting a hybride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The compounds of this invention can be regenerated from the base addition salts by the application or adaptation of known methods. For example, parent compounds of the invention can be regenerated from their base addition salts by treatment with an acid, e.g., hydrochloric acid.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

Compounds of the present invention may contain asymmetric centers. These asymmetric centers may independently be in either the R or S configuration. It will also be apparent to those skilled in the art that certain compounds of formula I may exhibit geometrical isomerism. Geometrical isomers include the cis and trans forms of compounds of the invention, i.e., compounds having alkenyl moieties or substituents on the ring systems. In addition, bicyclo ring systems include endo and exo isomers. The present invention comprises the individual geometrical isomers, stereoisomers, enantiomers and mixtures thereof.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The starting materials and intermediates are prepared by the application or adaptation of known methods, for example methods as described in the Reference Examples or their obvious chemical equivalents, or by methods described according to the invention herein.

The present invention is further exemplified but not limited by the following illustrative examples which describe the preparation of the compounds according to the invention.

Further, the following examples are representative of the processes used to synthesize the compounds of this invention.

EXAMPLE 1

2-(3-Fluorophenylamino)-6,7-diethoxyquinoxaline

To 0.25 g (0.989 mmol) of 2-chloro-6,7-diethoxyquinoxaline is added 2 mL of m-fluoraniline. This mixture is heated under nitrogen overnight to 120° C. The resting mixture is chromatographed (30:1 $CH_2Cl_2$:EtOH) to yield partially purified product. This solid is triturated with ethyl acetate to give 0.75 g of the product as a brownish yellow solid in 54.1% yield (m.p. 193° C.). Anal. Calcd for $C_{18}N_{18}N_3O_2F·0.25 H2O$: C, 65.15; H, 65.30; H, 5.30; N, 12.41.

EXAMPLE 2

2-Anilino-6-methoxy-quinoxaline hydrochloride

To 2-chloro-6-methoxy-quinoxaline (0.93 g, 4.8 mmol) under argon is added aniline (1.3 mL, 14.3 mmol). The reaction mixture is heated at 120° C. for 2 hours, then at 150° C. for 1.5 hours. The mixture is cooled and $CH_2Cl_2$ is added. The resulting suspension is stirred and the orange solid is filtered off, washed with $CH_2Cl_2/Et_2O$, then stirred vigorously in $H_2O$ for 40 minutes, filtered, and washed with $Et_2O$ to provide a bright-yellow solid.

The following compounds are prepared similarly beginning with the appropriate starting material.

2-(3-Carbamoylphenylamino)-6-methoxyquinoxaline, m.p. 247° C., Anal. Cald for $C_{16}N_{14}N_4O_2·0.25 H_2O$: C, 64.31; H, 4.89; N, 18.75. Found: C, 64.24; H, 5.04; N, 18.75;

2-(2-Fluorophenylamino)-6,7-diethoxyquinoxaline, m.p. 184° C ., Anal. Cald for $C_{18}H_{18}FN_3O_2$:C, 66.04; H, 5.54; F, 5.80; N, 12.84. Found: C, 65.75; H, 5.61; N, 12.68;

2-(3-Trifluoromethylphenylamino)-6,7-diethoxyquinoxaline, m.p. 158° C., Anal. Calcd for $C_{19}H_{18}F_3N_3O_2$: C, 60.47; H, 4.81; F, 15.10; N, 11.14. Found: C, 60.27; H, 4.84; N, 10.97;

(6-Methoxyquinoxalin-2-yl)-(3-methylphenyl)-amine, m.p. 133–135° C., Anal. Calcd for $C_{16}H_{15}N_3O$: C, 72.43; H, 5.70; N, 15.84. Found: C, 72.43; H, 5.79; N, 15.77.

6-Methoxy-2-phenylamino-quinoxaline; m.p. 152–153° C., Anal. Calcd for $C_{15}H_{13}N_3O$: C, 71.70; H, 5.21; N, 16.72. Found: C, 71.70; H, 5.16; N, 16.80;

2-Anilino-6-ethoxyquinoxaline, m.p. 118–120° C., Anal. Calcd for $C_{16}H_{15}N_3O·0.63 H_2O$: C, 69.48; H, 5.92; N, 15.19. Found: C, 69.24; H, 5.97; N, 15.14;

2-(3-Methoxyphenylamino)-6,7-diethoxyquinoxaline, m.p. 173° C. Anal. Calcd for $C_{19}H_{21}N_3O3$: C, 67.24; H, 6.24; N, 12.38. Found: C. 67.02; H, 6.23; N, 12.21;

2-(4-Fluorophenylamino)-6,7-diethoxyquinoxaline, m.p. 242° C., Anal. Calcd for $C_{18}H_{18}FN_3O_2·0.50 H_2O$: C, 64.27; H, 5.69; N, 12.49. Found: C, 64.21; H, 5.39; N, 12.24;

2-Phenylamino-6,7,-diethoxyquinoxaline, m.p. 239° C.;

(6,7-Dimethoxyquinoxalin-2-yl)-(3-fluorophenyl)-amine, m.p. 99–100° C. Anal. Calcd for $C_{16}H_{14}FN_3O_2$: C, 64.21; H, 4.71; F, 6.35; N, 14.04. Found: C, 64.35; H, 4.61; N, 13.84;

2-(3-Fluorophenylamino)-6,7-diethoxyquinoxaline, m.p. 193° C. Anal. Calcd for $C_{18}H_{18}FN_3O_2·0.25 H_2O$: C, 65.15; H, 5.62; N, 12.66. Found: C, 65.30; H, 5.30; N, 12.41;

(3-Bromophenyl)-(6,7-dimethoxyquinoxalin-2-yl)-amine, m.p. 197–198° C., Anal. Calcd for $C_{16}H_{14}BrN_3O_2$: C, 53.35; H, 3.92; Br, 22.18; N, 11.67. Found: C, 53.39; H, 3.82; N, 11.64;

(6,7-Dimethoxyquinoxalin-2-yl)-phenyl-amine, m.p. 88–90° C., Anal. Calcd for $C_{16}H_{15}N_3O_2$: C, 68.31; H, 5.37; N, 14.94. Found: C, 68.02; H, 5.52; N, 14.91; and (3-Chlorophenyl)-(6,7-dimethoxyquinoxalin-2-yl)-amine, m.p. 187–188° C., Anal. Calcd for $C_{18}H_{14}ClN_3O_2$: C, 60.86; H, 4.47; Cl, 11.23; N, 13.31. Found: C, 60.85; H, 4.59; N, 13.26.

EXAMPLE 3

2-Benzylamino-6,7-diethoxyquinoxaline

To 0.3 g (1.19 mmol) of 2-chloro-6,7-diethoxyquinoxaline is added 2 mL of benzylamine. This mixture is heated under nitrogen overnight to 120° C. The resulting mixture is partitioned between $CH_2Cl_2$ and saturated $NaHCO_3$ solution. The organic layer is concentrated, and the residue chromatographed (30.1 $CH_2Cl_2$:EtOH) to provide 0.337 g of the product as a yellow solid in 87.6% yield (m.p. 136° C.). Anal. Calcd for $C_{19}H_{21}N_3O_2$: C, 70,57, H, 6.54; N, 12.99. Found: C, 70.54; H, 6.66; N, 12.80.

The following compounds are prepared similarly beginning with the appropriate starting materials.

(3-Bromobenzyl)-(6,7-dimethoxyquinoxalin-2-yl)-amine, m.p. 199–206° C., Anal. Calcd for $C_{17}H_{16}BrN_3O_2$: C, 54.56; H, 4.31; Br, 21.35; N, 11.23. Found: C, 49.90; H, 4.00; N, 10.14;

Benzyl-(6.7-dimethoxyquinoxalin-2-yl)-amine, m.p. 210–214° C., Anal. Calcd for $C_{17}H_{17}N_3O_2$: C, 69.14; H, 5.80; N, 14.23. Found; C, 61.78; H, 5.47; N, 12.64; and 2-Benzylamino)-6,7-diethioxyquinoxaline, n.p. 136° C., Anal. Calcd for $C_{19}H_{21}N_3O_2$: C, 70.57; H, 6.55; N, 12.99. Found: C, 70.54; H, 6.66; N; 12.80.

EXAMPLE 4

2-((R)-α-Methylbenzylamino-6,7-diethoxyquinoxaline

To 0.3 g (1.19 mmols) of 2-chloro-6,7-diethoxyquinoxaline is added 2 mL of (R)-(+)-α-methylbenzylamine. This mixture is heated for three days under nitrogen to 120° C. The resulting mixture is partitioned between $CHCl_3$ and saturated $NaHCO_3$ solution. The organic layer is concentrated, and the residue chromatographed (30:1 $CH_2Cl_2$:EtOH) to provided 0.118 g of the product as a yellow solid in 29.4% yield (m.p. 53–56° C). Anal. Calc for $C_{20}H_{23}N_3O_2$·0.25 H2O: C. 70.26; H, 6.93; N, 12.29. Found C, 70.56; H, 6.80; N, 12.35.

The following compound is prepared similarly beginning with the appropriate starting materials.

2-((S)-α-Methylbenzyl-amino)-6,7-diethoxyquinoxaline, m.p. 55–58° C., Anal. Calcd for $C_{20}H_{23}N_3O_2$·0.25 $H_2O$: C, 70.26; H, 6.93; N, 12.29. Found: C. 70.49; H, 6.89; N, 12.23.

EXAMPLE 5

2,7-Bis-cyclohexyloxy-6-methoxy-quinoxaline

To a DMF solution (5 mL) of NaH (0.32 g, 8 mmol) under argon, cyclohexanol (0.7 mL, 6.7 mmol) is added dropwise. The mixture is stirred at room temperature for 25 minutes, then 2-chloro-6,7-dimethoxyquinoxaline is added portionwise. The reaction is stirred for 15 minutes at room temperature, at 90° C. for 2 hours, and at 110° C. for 1 hour. The mixture is cooled, quenched with $H_2O$ and partitioned between EtOAc/$H_2O$. The organic layer is washed with $H_2O$ and brine, dried ($MgSO_4$), and chromatographed (10% EtOAc/hexanes) to provide a way white solid (m.p. 75–78° C.). Anal. Calcd. for $C_{21}H_{28}N_2O_3$: C, 70.76; H, 7.92; N, 7.86; Found: C. 70.81; H, 7.79; N, 7.70.

The following compounds are prepared similarly beginning with the appropriate starting materials.

2-Phenoxy-6-methoxyquinoxaline, m.p. 79–81° C.; and 6,7-Diethoxy-2-phenoxyquinoxaline, m.p. 130–131° C., Anal. Calcd for C18H18N2O3: C, 69.66; H, 5.85; N, 9.03. Found: C, 69.53; H, 5.82; N, 8.91.

EXAMPLE 6

Cyclohexyl-(6,7-dimethoxyquinoxalin-2-ylmethyl)-amine

To a 0.067 M solution of 6,7-dimethoxy-2-quinoxaline carboxaldehyde in 2:1 MeOH/1,2-dichlorethane (7.5 mL, 0.5 mmol) is added cyclohexylamine (0.11 mL, 0.9 mmol). The reaction is allowed to stir at room temperature overnight, then NaBH4 (0.038 g, 1 mmol) is added and the reaction mixture is stirred overnight. The mixture is then concentrated and chromatographed (50% EtOAc/hexanes—approximately 5% MeOH in 50% EtOAc/hexanes). The oil is dissolved in EtOAc/hexanes and treated with HCl in EtOH. The resulting solution is concentrated and the solids are triturated with isopropanol to provide a white solid after drying in vacuo at 60° C. (m.p. 185–190° C. dec.). Anal. Calcd. for C17H23N3O2·HCl: C, 60.44; H, 17.16; N, 12.44; Found: C, 60.48; H, 6.88; N, 12.07.

EXAMPLE 7

Cyclohexyl-(6-methoxy-7-morpholin-4-yl-quinoxalin-2-yl)-amine

This preparation is based on a adaptation of the method described by Buchwald, et al, J. Am. Chem. Soc., 1996, 118, 7215. To a toluene solution of 2-cyclohexylamino-6-methoxy-7-bromo-quinoxaline (0.1 g, 0.3 mmol) under argon is added morpholine (0.1 g, 0.3 mmol), sodium tert-butoxide (0.04 g, 0.42 mmol, S-(–)-BINAP (cat., 0.001 g), and Pd(dba)2 (cat., 0.001 g). The reaction mixture is heated to 80° C. overnight. The mixture is cooled, dilute with Et2O, filtered, concentrated, and chromatographed (50% EtOAc/hexanes). The product is recrystallized from EtOAc/hexanes to provide, in two crops, to provide a yellow solid (m.p. 194–196° C.). Anal Calcd. for C19H26N4O2C:, 66.64; H, 7.65; N, 16.36; Found: C, 66.60; H, 7.60; N, 16.51.

EXAMPLE 8

3-Cyclohexyloxy-6,7-dimethoxyquinoline

To a THF solution (30 mL) at 0° C. is added 3-hydroxy-6,7-dimethoxyquinoline (0.237 g, 1.15 mmol), cyclohexanol (0.347 g, 3.46 mmol), Ph3P (0.908 g, 3.46 mmol). Diethylazodicarboxylate is added portionwise until the solution retained a deep red color (0.663 g, 3.81 mmol). After 4 hours the solution is concentrated and the residue chromatographed (50% EtOAc in hexanes). The product is recrystallized from isopropanol/hexanes as the HCl salt as a white solid (m.p. 229–232° C., dec.).

EXAMPLE 9

2-Anilino-6-quinoxalinol

By the method of Feutrill, G. I.; Mirrington, R. N. Tet. Lett. 1970, 1327; the aryl methyl ether is converted to the phenol derivative. To 2-anilino-6-methoxy-quinoxaline (0.27 g, 1.07 mmol) under argon in DMF is added the sodium salt of ethanethiol (0.19 g, 2 mmol). The reaction mixture is heated to 110° C. overnight. The mixture is concentrated and partitioned between EtOAc and $H_2O$/5% tartaric acid such that the pH of the aqueous layer is approximately 4. The organic layer is washed with $H_2O$ (4x), then with 2.5% NaOH (4x). The basic layers combined, washed with EtOAc (2x), are-acidified with 5% tartaric acid, and washed with multiple portions of EtOAc. The organic layers are combined, washed with brine, dried ($Na_2SO_4$), and concentrated. The resulting solid is chromatographed (50% EtOAc/hexanes). An analytical sample is obtained by triturating the product with $Et_2O$ to provide a yellow powder (m.p. 211–213° C.). Anal. Calc. for $C_{14}H_{11}N_3O$: C, 70.88; H, 4.67; N, 17.71; Found: C. 70.64; H, 4.85; N, 17.58.

EXAMPLE 10

Phenyl-[6-(tetrahydrofuran-3-(R)-yl-oxy)quinoxalin-2-yl]amine

To a THF solution of 10° C. under argon is added 2-anilino-6-quinoxalinol (0.23 g, 0.97 mmol), (S)-(+)-3-hydroxytetrahydrofuran (0.086 mL, 1.3 mmol), and triphenylphosphine (0.31 g, 1.2 mmol). DEAD (0.18 mL, 1.2 mmol) is added portionwise. The reaction is allowed to warm to room temperature and stirred for 1.5 hours. The mixture is concentrated and partitioned between EtOAc and $H_2O$. The organic layer is washed with $H_2O$, brine, dried ($MgSO_4$), and concentrated. The resulting yellow oil is chromatographed (50% EtOAc/hexanes) and taken up in $Et_2O$/IPA (isopropanol). $HCl/Et_2O$ solution is added dropwise and the resulting red-orange powder is dried in vacuo. The powder is free-based by stirring in MeOH with washed (3×$H_2O$, 5× MeOH) basic ion exchange resin. The mixture is stirred 30 minutes, filtered, concentrated, and recrystallized from EtOAc/hexanes to provide, in two crops, the product (m.p. 173–175° C.). Anal. Calcd. for $C_{18}H_{17}N_3O_2$: C, 70.35; H, 5.57; N, 13.67; Found: C, 70.19; H, 5.60; N, 13.66.

EXAMPLE 11

2-Anilino-6isopropoxy-quinoxaline hydrochloride

To NaH (0.033 g, 0.84 mmol) under argon is added 1 mL DMF. 2-Anilino-6-quinoxalinol (0.1 g, 0.42 mmol) in 1.5 mL DMF is added portionwise. After 30 minutes, 2-bromopropane is added dropwise and the solution is heated to 50° C. for 1.5 hours. The cooled reaction mixture is quenched with water and partitioned between EtOAc and $H_2O$, washed with $H_2O$ (3×), brine, dried ($MgSO_4$), and concentrated. The resulting residue is chromatographed (30% EtOAc/hexanes) to provide 0.05 g dialkylated product and 0.1 g of the title compound. An analytical sample of the HCl salt is obtained by addition of IPA/HCl to an $Et_2O$/IPA solution of the free base to provide HCl salt (m.p. 205–210° C. dec). Anal. Calcd. for $C_{17}H_{17}N_3O \cdot HCl$: C, 64.65; H, 5.74; N, 13.31; Found: C, 64.51; H, 5.90; N, 13.09.

EXAMPLE 12

3-Cyclohexyloxy-6,7-dimethoxyquinoxaline 1-oxide.

A mixture of 2-cyclohexyloxy-6,7-dimethoxyquinoxaline (110 mg, 0.38 mmol) and metachlorobenzoic peracid (70%, 113 mg, 0.46 mmol) in 10 mL of methylene chloride is stirred at room temperature for one day. The solution after filtration is concentrated and the residue is chromatographed on silica gel (20% ethyl acetate/hexane) to provide the desired product (m.p. 167–169° C.). trans-4-(6,7-Dimethoxy-4-oxy-quinoxalin-2-ylamino)-cyclohexanol (m.p. 220–222° C.) is prepared similarly, Anal. Calcd. for $C_{16}H_{21}N_3O_4 \cdot 0.2 H_2O$: C, 59.42; H, 6.69; N, 12.99; Found: C, 59.43; H, 6.64; N, 12.95.

INTERMEDIATE EXAMPLE 1

4-Bromo-5-methoxy-benzene-1,2-diamine dihydrochloride

To a solution of EtOAc (50 mL) and 5-bromo-4-methoxy-2-nitro-phenylamine (2.5 g, 10 mmol) under argon is added 5% Pd/C (0.5 g). The reaction mixture is hydrogenated at 50 psi for 1 hour. The mixture is filtered through Celite into a solution of HCl/IPA/EtOAc, and the pad is washed with additional EtOAc. The resulting precipitate is filtered off to provide white solid.

INTERMEDIATE EXAMPLE 2

7-Bromo-6-methoxy-quinoxalin-2-ol and 6-Bromo-7-methoxy-quinoxalin-2-ol

To a solution of MeOH (15 mL) under argon pulverized NaOH pellets (0.86 g, 21 mmol) and 4-bromo-5-methoxy-benzene-1,2-diamine dihydrochloride (2.7 g, 9.3 mmol). The mixture is stirred for 10 minutes; then a solution of 45% ethyl gloxylate in toluene (2.7 g, 12 mmol) is added portionwise. The reaction mixture is refluxed for 1 hour, then cooled. Water is added, then the suspension is filtered. The resulting solid is washed successively with $H_2O$, MeOH, IPA, and $Et_2O$ to provide a yellow powder.

INTERMEDIATE EXAMPLE 3

7-Bromo-2-chloro-6-methoxy-quinoxaline and 6-Bromo-2-chloro-7-methoxy-quinoxaline To a mixture of 7-bromo-6-methoxy-quinoxalin-2-ol and 6-bromo-7-methoxy-quinoxalin-2-ox (1 g, 3.9 mmol is added $POCl_3$ (5 mL). The reaction mixture is refluxed 1 hour, poured into ice water, filtered, then washed with water to provide a light-tan solid. Ratio of 7-bromo-2-chloro-6-methoxy-quinoxaline: 6-bromo-2-chloro-7-methoxy-quinoxaline is approximately 7:1 by $^1H$ NMR.

INTERMEDIATE EXAMPLE 4

5-Chloro-4-methoxy-2-nitroaniline

To a solution of N-(5-chloro-4-methoxy-2-nitrophenyl)-acetamide (2 g, 8.2 mmol) in 5N HCl (20 mL) is added 1,4-dioxane (10 mL), and the mixture is stirred at 60° C. for 1.5 hours. The reaction mixture is concentrated and partitioned between EtOAc/2 N NaOH. The aqueous layers are washed with EtOAc (3×), brine, dried ($MgSO_4$), adsorbed onto silica gel, and chromatographed (70% EtOAc/hexanes) to provide an orange powder.

INTERMEDIATE EXAMPLE 5

4-Chloro-5-methoxy-benzene-1,2-diamine dihydrochloride

To a solution of EtOAc (25 mL) and 5-chloro-4-methoxy-2-nitro-phenylamine (1.6 g, 7.9 mmol) under argon is added 5% Pd/C (0.5 g). The reaction mixture is hydrogenated at 50 psi for 1 hour. The mixture is filtered under $N_2$ through Celite into a solution of 1 N $HCl/Et_2O$ in EtOAc, and the pad is washed with additional EtOAc. The resulting precipitate is filtered off to provide a white solid.

INTERMEDIATE EXAMPLE 6

7-Chloro-6-methoxy-quinoxalin-2 ol and 6-Chloro-7-methoxy-quinoxalin-2-ol

To a solution of 4-chloro-5-methoxy-benzene-1,2-diamine dihydrochloride (1.8 g, 7.2 mmol) in EtOH (15 mL) under argon is added TEA (2.5 mL, 18 mmol) at 0° C. The mixture is stirred for 20 minutes, then a solution of 45% ethyl glyoxylate in toluene (2.1 g, 9.3 mmol) is added portionwise. The reaction mixture is warmed to room temperature, refluxed for 1.5 hour, then cooled, water is added, then the suspension is filtered and washed successively with $H_2O$, IPA, and $Et_2O$ to provide a light-yellow powder. The product is azeotroped several times with toluene and dried in vacuo before use.

INTERMEDIATE EXAMPLE 7

2,7-Dichloro-6-methoxy-quinoxaline and 2,6-Dichloro-7-methoxy-quinoxaline

To a mixture of 7-chloro-6-methoxy-quinoxalin-2-ol and 6-chloro-7-methoxy-quinoxalin-2-ol (1 g, 4.7 mmol) under a $CaCl_2$ drying tube is added $POCl_3$ (5 mL). The reaction mixture is refluxed 30 minutes, poured into cold saturated $NaHCO_3$ solution, filtered, then washed with water to provide a solid. The ratio of 2,7-dichloro-6-methoxy-quinoxaline: 2,6-dichloro-7-methoxy-quinoxaline is approximately 6:1 by $^1H$ NMR.

The compounds of formula I as described herein inhibit inhibition of cell proliferation and/or cell matrix production and/or cell movement (chemotaxis) via inhibition of PDGF-R tyrosine kinase activity. A large number of disease states are caused by either uncontrolled reproduction of cells or overproduction of matrix or poorly regulated programmed cell death (apoptosis). These disease states involve a variety of cell types and include disorders such as leukemia, cancer, glioblastoma, psoriasis, inflammatory disease, bone diseases, fibrotic diseases, atherosclerosis and occurring subsequent to angioplasty of the coronary, femoral or kidney arteries or, fibroproliferative disease such as in arthritis, fibrosis of the lung, kidney and liver. In particular, PDGF and PDGF-R have been reported to be implicated in specific types of cancers and tumors such as brain cancer, ovarian cancer, colon cancer, prostate cancer lung cancer, Kaposi's sarcoma and malignant melanoma. In addition, deregulated cellular proliferative conditions follow from coronary bypass surgery. The inhibition of tyrosine kinase activity is believed to have utility in the control of uncontrolled reproduction of cells or overproduction of matrix or poorly regulated programmed cell death (apoptosis).

This invention relates to the modulation and/or inhibition of cell signaling, cell proliferation and/or cell matrix production and/or cell movement (chemotaxis), the control of abnormal cell growth and cell inflammatory response. More specifically, this invention relates to the use of substituted quinoline and quinoxaline compounds which exhibit selective inhibition of differentiation, proliferation, matrix production, chemotaxis or mediator release by effectively inhibiting platelet-derived growth factor-receptor (PDGF-R) tyrosine kinase activity.

Initiation of autophosphorylation, i.e., phosphorylation of the growth factor receptor itself, and of the phosphorylation of a host of intracellular substrates are some of the biochemical events which are involved in cell signaling, cell proliferation, matrix production, chemotaxis and mediator release.

By effectively inhibiting Lck tyrosine kinase activity, the compounds of this invention are also useful in the treatment of resistance to transplantation and autoimmune diseases such as rheumatoid arthritis, multiple sclerosis and systemic lupus erythematosus, in transplant rejection, in graft vs. host disease, in hyperproliferative disorders such as tumours and psoriasis, and in diseases in which cells receive proinflammatory signals such as asthma, inflammatory bowel disease and pancreatitis. In the treatment of resistance to transplantation, a compound of this invention may be used either prophylactically or in response to an adverse reaction by the human subject to a transplanted organ or tissue. When used prophylactically, a compound of this invention is administered to the patient or to the tissue or organ to be transplanted in advance of the transplantation operation. Prophylactic treatment may also include administration of the medication after the transplantation operation but before any signs of adverse reaction to transplantation are observed. When administered in response to an adverse reaction, a compound of this invention is administered directly to the patient in order to treat resistance to transplantation after outward signs of the resistance have been manifested.

According to a further feature of the invention there is provided a method of inhibiting PDGF tyrosine kinase activity comprising contacting a compound according to claim 1 with a composition containing a PDGF tyrosine kinase.

According to a further feature of the invention there is provided method of inhibiting Lck tyrosine kinase activity comprising contacting a compound according to claim 1 with a composition containing a Lck tyrosine kinase.

According to a further feature of the invention there is provided a method for the treatment of a patient suffering from, or subject to, conditions which may be ameliorated or prevented by the administration of an inhibitor of PDGF-R tyrosine kinase activity and/or Lck tyrosine kinase activity, for example conditions as hereinbefore described, which comprises the administration to the patient of an effective amount of compound of formula I or a composition containing a compound of formula I, or a pharmaceutically acceptable salt thereof.

Reference herein to treatment should be understood to include prophylactic therapy as well as treatment of established conditions.

The present invention also includes within its scope pharmaceutical compositions which comprise pharmaceutically acceptable amount of at least one of the compounds of formula I in association with a pharmaceutically acceptable carrier, for example, an adjuvant, diluent, coating and excipient.

In practice compounds or compositions for treating according to the present invention may administered in any variety of suitable forms, for example, by inhalation, topically, parenterally, rectally or orally; more preferably orally. More specific routes of administration include intravenous, intramuscular, subcutaneous, intraocular, intrasynovial, colonical, peritoneal, transepithelial including transdermal, ophthalmic, sublingual, buccal, dermal, ocular, nasal inhalation via insufflation, and aerosol.

The compounds of formula I may be presented in forms permitting administration by the most suitable route and the invention also relates to pharmaceutical compositions containing at least one compound according to the invention which are suitable for use as a medicament in a patient. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixers or syrups, and may contain one or more agents chosen from the group comprising sweeteners such as sucrose, lactose, fructose, saccharin or Nutrasweet®, flavorings such as peppermint oil, oil of wintergreen, or cherry or orange flavorings, colorings, or stabilizers such as methyl- or propyl-paraben in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silica gels combined with lubricants such as magnesium stearate, sodium lauryl sulfate and talc may be used for preparing tablets, troches, pills, capsules and the like. To prepare a capsule, it is advantageous to use lactose and liquid carrier, such as high molecular weight polyethylene glycols. Various other materials may be present as coatings or to otherwise modify the physical form of the dosage unit. For instance, tablets, pills, or capsules may be coated with shellac, sugar or both. When aqueous suspensions are used they may contain emulsifying agents or agents which facilitate suspension. Diluents such as sucrose, ethanol, polyols such as polyethylene glycol, propylene glycol and glycerol, chloroform or mixtures thereof may also be used. In addition, the active compound may be incorporated into sustained-released preparations and formulations.

For oral administration, the active compound may be administered, for example, with an inert diluent or with an assimilable edible carrier, or it may be enclosed in hard or soft shell gelatin capsules, or it may be compressed into tablets, or it may be incorporated directly with the food of the diet, or may be incorporated with excipient and used in the form of ingestible tablets, buccal tablets, troches, capsules, elixers, suspensions, syrups, wafers, and the like.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the active compound as a free base or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yields a powder of the active ingredient plus any additional desired ingredient from previously sterile-filtered solution thereof.

Topical administration, gels (water or alcohol based), creams or ointments containing compounds of the invention may be used. Compounds of the invention may be also incorporated in a gel or matrix base for application in a patch, which would allow a controlled release of compound through transdermal barrier.

For administration through inhalation, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

Compositions according to the invention may also be formulated in a manner which resists rapid clearance from the vascular (arterial or venous) wall by convection and/or diffusion, thereby increasing the residence time of the viral particles at the desired site of action. A periadventitial depot comprising a compound according to the invention may be used for sustained release. One such useful depot for administering a compound according to the invention may be a copolymer matrix, such as ethylene-vinyl acetate, or a polyvinyl alcohol gel surrounded by a Silastic shell. Alternatively, a compound according to the invention may be delivered locally from a silicone polymer implanted in the adventitia.

An alternative approach for minimizing washout of a compound according to the invention during percutaneous, transvascular delivery comprises the use of nondiffusible, drug-eluting microparticles. The microparticles may be comprised of a variety of synthetic polymers, such as polylactide for example, or natural substances, including proteins of polysaccharides. Such microparticles enable strategic manipulation of variables including total dose of drug and kinetics of its release. Microparticles can be injected efficiently into the arterial or venous wall through a porous balloon catheter or a balloon over stent, and are retained in the vascular wall and the periadventitial tissue for at least about two weeks. Formulations and methodologies for local, intravascular site-specific delivery of therapeutic agents are discussed in Reissen et al. (*J. Am. Coll. Cardiol.* 1994; 23: 1234–1244), the entire contents of which are hereby incorporated by reference.

A composition according to the invention may also comprise a hydrogel which is prepared from any biocompatible or non-cytotoxic (homo or hetero) polymer, such as a hydrophilic polyacrylic acid polymer that can act as a drug absorbing sponge. Such polymers have been described, for example, in application WO93/08845, the entire contents of which are hereby incorporated by reference. Certain of them, such as, in particular, those obtained from ethylene and/or propylene oxide are commercially available.

In the use of compounds according to the invention for treating pathologies which are linked to hyperproliferative disorders, the compounds according to the invention can be administered in different ways. For the treatment of restenosis, the compounds of the invention are administered directly to the blood vessel wall by means of an angioplasty balloon which is coated with a hydrophilic film (for example a hydrogel) which is saturated with the compound, or by means of any other catheter containing an infusion chamber for the compounds, which can thus be applied in a precise manner to the site to be treated and allow the compound to be liberated locally and efficiently at the location of the cells to be treated. This method of administration advantageously makes it possible for the compound to contact quickly the cells in need of treatment.

The treatment method of the invention preferably consists in introducing a compound according to the invention at the site to be treated. For example, a hydrogel containing composition can be deposited directly onto the surface of the tissue to be treated, for example during a surgical intervention. Advantageously, the hydrogel is introduced at the desired intravascular site by coating a catheter, for example a balloon catheter, and delivering to the vascular wall, preferably at the time of angioplasty. In a particularly advantageous manner, the saturated hydrogel is introduced at the site to be treated by means of a balloon catheter. The balloon may be chaperoned by a protective sheath as the catheter is advanced toward the target vessel, in order to minimize drug washoff after the catheter is introduced into the bloodstream.

Another embodiment of the invention provides for a compound according to the invention to be administered by means of perfusion balloons. These perfusion balloons, which make it possible to maintain a blood flow and thus to decrease the risks of ischaemia of the myocardium, on inflation of the balloon, also enable the compound to be delivered locally at normal pressure for a relatively long time, more than twenty minutes, which may be necessary for its optimal action. Alternatively, a channelled balloon catheter ("channelled balloon angioplasty catheter", Mansfield Medical, Boston Scientific Corp., Watertown, Mass.) may be used. The latter consists of a conventional balloon covered with a layer of 24 perforated channels which are perfused via an independent lumen through an additional infusion orifice. Various types of balloon catheters, such as double balloon, porous balloon, microporous balloon, channel balloon, balloon over stent and hydrogel catheter, all of which may be used to practice the invention, are disclosed in Reissen et al. (1994), the entire contents of which are hereby incorporated by reference.

The use of a perfusion balloon catheter is especially advantageous, as it has the advantages of both keeping the balloon inflated for a longer period of time by retaining the properties of facilitated sliding and of site-specificity of the hydrogel, are gained simultaneously.

Another aspect of the present invention relates to a pharmaceutical composition comprising a compound according to the invention and poloxamer, such as Poloxamer 407 is a non-toxic, biocompatible polyol, commercially available (BASF, Parsippany, N.J.).

A poloxamer impregnated with a compound according to the invention may be deposited directly on the surface of the tissue to be treated, for example during a surgical intervention. Poloxamer possesses essentially the same advantages as hydrogel while having a lower viscosity.

The use of a channel balloon catheter with a poloxamer impregnated with a compound according to the invention is especially advantageous. In this case, the advantages of both keeping the balloon inflated for a longer period of time, while retaining the properties of facilitated sliding, and of site-specificity of the poloxamer, are gained simultaneously.

The percentage of active ingredient in the compositions of the invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics which can influence the efficacy of the compound according to the invention.

The compounds/compositions according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for other patients, it will be necessary to prescribe not more than one or two doses per day.

The compounds of the present invention may also be formulated for use in conjunction with other therapeutic agents such as agents of in connection with the application of therapeutic techniques to address pharmacological conditions which may be ameliorated through the application of a compound of formula I, such as in the following:

The compounds of the present invention may be used in the treatment of restenosis post angioplasty using any device such as balloon, ablation or laser techniques. The compounds of the present invention may be used in the treatment of restenosis following stent placement in the vasculature either as 1) primary treatment for vascular blockage, or 2) in the instance where angioplasty using any device fails to give a patent artery. The compounds of the present invention may be used either orally, by parenteral administration or the compound could be applied topically through the intervention of a specific device or as a properly formulated coating on a stent device.

For topical application as a coating on a stent device, the coated stent device is prepared by applying polymeric material in which the compound of the invention is incorporated to at least one surface of the stent device.

Polymeric materials suitable for incorporating the compound of the invention include polymers having relatively low processing temperatures such as polycaprolactone, poly (ethylene-co-vinyl acetate) or poly(vinyl acetate or silicone gum rubber and polymers having similar relatively low processing temperatures. Other suitable polymers include non-degradable polymers capable of carrying and delivering therapeutic drugs such as latexes, urethanes, polysiloxanes, styrene-ethylene/butylene-styrene block copolymers (SEBS) and biodegradable, bioabsorbable polymers capable of carrying and delivering therapeutic drugs, such as poly-DL-lactic acid (DL—PLA), and poly-L-lactic acid (L—PLA), polyorthoesters, polyiminocarbonates, aliphatic polycarbonates, and polyphosphazenes.

A porosigen may also be incorporated in the drug loaded polymer by adding the porosigen to the polymer along with the therapeutic drug to form a porous, drug loaded polymeric membrane. "Porosigen" means as any moiety, such as microgranules of sodium chloride, lactose, or sodium heparin, for example, which will dissolve or otherwise be degraded when immersed in body fluids to leave behind a porous network in the polymeric material. The pores left by such porosignes can typically be as large as 10 microns. The pores formed by porosignes such as polyethylene glycol (PEG), polyethylene oxide/polypropylene oxide (PEO/PPO) copolymers, for example, can also be smaller than one micron, although other similar materials which form phase separations from the continuous drug loaded polymeric matrix and can later be leached out by body fluids can also be suitable for forming pores smaller than one micron. The polymeric material can be applied to the stent while the therapeutic drug and porosigen material are contained within the polymeric material, to allow the porosigen to be dissolved or degraded by body fluids when the stent is placed in a blood vessel, or alternatively, the porosigen can be dissolved and removed from the polymeric material to form pores in the polymeric material prior to placement of the polymeric material combined with the stent within a blood vessel.

If desired, a rate-controlling membrane can also be applied over the drug loaded polymer, to limit the release rate of the compound of the invention. The rate-controlling membrane can be added by applying a coating form a solution, or a lamination. The rate-controlling membrane applied over the polymeric material can be formed to include a uniform dispersion of a porosigen in the rate-controlling membrane, and the porosigen in the rate-controlling membrane can be dissolved to leave pores in the rate-controlling membrane typically as large as 10 microns, or as small as 1 micron, for example, although the pores can also be smaller than 1 micron. The porosigen in the rate-controlling membrane can be, for example sodium chloride, lactose, sodium heparin, polyethylene glycol, polyethylene oxide/polypropylene oxide copolymers, and mixtures thereof.

In another aspect, the coating on the stent device can be formed by applying the compound of the invention to at least one surface of the stent device to form a bioactive layer and then applying one or more coats of porous polymeric material over the bioactive layer, such that the porous polymeric material has a thickness adequate to provide a controlled release of the compound.

The porous polymeric material is composed of a polyamide, parylene or a parylene derivative which is applied to the stent device by catalyst-free vapor deposition. "Parylene" refers to a polymer based on p-xylylene and made by vapor phase polymerization as described in U.S. Pat. No. 5,824,049, incorporated herein by reference.

Alternatively, the porous polymeric material is applied by plasma deposition. Representative polymers suitable for plasm deposition include poly(ethylene oxide), poly (ethylene glycol), poly(propylene oxide), and polymers of methane, silicone, tetrafluoroethylene tetramethyldisiloxane, and the like.

Other suitable polymer systems include polymers derived from photopolymerizable monomers such as liquid monomers preferably having at least two cross linkable C—C (Carbon to Carbon) double bonds, and being a non-gaseous addition polymerizable ethylenically unsaturated compound, having a boiling point above 100° C., at atmospheric pressure, a molecular weight of about 100–1500 and being capable of forming high molecular weight addition polymers readily. More preferably, the monomer is preferably an addition photopolymerizable polyethylenically unsaturated acrylic or methacrylic acid ester containing two or more acrylate or methacrylate groups per molecule or mixtures thereof. Representative examples of such multifunctional acrylates are ethylene glycol diacrylate, ethylene glycol dimethacrylate, trimethylopropane triacrylate, trimethylopropane trimethacrylate, pentaerythritol tetraacrylate or pentaerythritol tetramethacrylate, 1,6-hexanediol dimethacrylate, and diethyleneglycol dimethacrylate.

Also useful in some special instances are monoacrylates such as n-butyl-acrylate, n-butyl methacrylate, 2-ethylhexyl acrylate, lauryl-acrylate, and 2-hydroxy-propyl acrylate. Small quantities of amides of (meth)acrylic acid such as N-methylol methacrylamide butyl ether are also suitable, N-vinyl compounds such as N-vinyl pyrrolidone, vinyl esters of aliphatic monocarboxylic acids such as vinyl oleate, vinyl ethers of diols such as butanediol-1,4-divinyl ether and allyl ether and allyl ester are also suitable. Also included are other monomers such as the reaction products of di- or polyepoxides such as butanediol-1,4-diglycidyl ether or bisphenol A diglycidyl ether with (meth)acrylic acid. The characteristics of the photopolymerizable liquid dispersing medium can be modified for the specific purpose by a suitable selection of monomers or mixtures thereof.

Other useful polymer systems include a polymer that is biocompatible and minimizes irritation to the vessel wall when the stent is implanted. The polymer may be either a biostable or a bioabsorbable polymer depending on the desired rate of release or the desired degree of polymer stability. Bioabsorbable polymers that could be used include poly(L-lactic acid), polycaprolactone, poly(lactide-co-glycolide), poly(hydroxybutyrate), poly (hydroxybutyrate-co-valerate), polydioxanone, polyorthoester, polyanhydride, poly(glycolic acid), poly(D,L-lactic acid), poly(glycolic acid-cotrimethylene carbonate), polyphosphoester, polyphosphoester urethane, poly(amino acids), cyanoacrylates, poly(trimethylene carbonate), poly (iminocarbonate), copoly(ether-esters) (e.g., PEO/PLA), polyalkylene oxlates, polyphoosphazenes and biomolecules such as fibrin, fibrinogen, cellulose, starch, collagen and hyaluronic acid. Also, biostable polymers with a relatively low chronic tissue response such as polyurethanes, silicones, and polyesters could be used and other polymers could also be used if they can be dissolved and cured or polymerized on the stent such as polyolefins, polyisobutylene and ethylene-alphaolefine copolymers; acrylic polymers and copolymers, vinyl halide polymers and copolymers, such as polyvinyl chloride; polyvinyl ethers, such as polyvinyl methyl esther; polyvinylidene halides, such as polyvinylidene fluoride and polyvinylidene chloride; polyacrylonitrile, polyvinyl ketones, polyvinyl aromatics, such as polstyrene, polyvinyl esters, such as polyvinyl acetate; copolymers of vinyl monomers with each other and olefins, such as ethylene-methyl methacrylate copolymers, acrylonitril-styrene copolyers, ABS resins, and ethylene-vinyl acetate copolymers; polyamides, such as Nylone 66 and polycaprolactam; alkyl reins, polycarbonates; polyoxymethylenes; polyimides, polyethers; opoxy reins, polyurethanes; rayon-triacetate; cellulose, cellulose acetate, cellulose butyrate; cellulose acetate buryrate; cellophane, cellulose nitrate; cellulose propionate; cellulose ethers; and carboxymethyl cellulose.

In addition to plasma deposition and vapor phase deposition, other techniques for applying the various coatings on the stent surfaces may be employed. For example, a polymer solution may be applied to the stent and the solvent allowed to evaporate, thereby leaving on the stent surface a coating of the polymer and the therapeutic substance. Typically, the solution can be applied to the stent by either spraying the solution onto the stent or immersing the stent in the solution. The compounds of the present invention may be used in the treatment of restenosis in combination with any anticoagulant, antiplatelet, antithrombotic or profibrinolytic agent. Often patients are concurrently treated prior, during and after interventional procedures with agents of these classes either in order to safely perform the interventional procedure or to prevent deleterious effects of thrombus formation. Some examples of classes of agents known to be anticoagulant, antiplatelet, antithrombotic or profibrinolytic agents include any formulation of heparin, low molecular weight heparins, pentasaccharides, fibrinogen receptor antagonists, thrombin inhibitors, Factor Xa inhibitors, or Factor VIIa inhibitors.

The compounds of the present invention may be used in combination with any antihypertensive agent or cholesterol or lipid regulating agent in the treatment of restenosis or atherosclerosis concurrently with the treatment of high blood pressure or antherosclerosis. Some examples of agents that are useful in the treatment of high blood pressure include compounds of the following classes; beta-blockers, ACE inhibitors, calcium channel antagonists and alpha-receptor antagonists. Some examples of agents that are useful in the treatment of elevated cholesterol levels or disregulated lipid levels include compounds known to be HMGCoA reductase inhibitors, compounds of the fibrate class, The compounds of the present invention may be used in the treatment of various forms of cancer either alone or in combination with compounds known to be useful in the treatment of cancer.

It is understood that the present invention includes combinations of compounds of the present invention with one or more of the aforementioned therapeutic class agents Compounds within the scope of the present invention exhibit marked pharmacological activities according to tests described in the literature which tests results are believed to correlate to pharmacological activity in humans and other mammals. The following pharmacological in vitro and in vivo test results are typical for characterizing compounds of the present invention.

Preparation of Pharmaceutical Compositions and Pharmacological Test Section

Compounds within the scope of this invention exhibit significant activity as protein tyrosine kinase inhibitors and possess therapeutic value as cellular antiproliferative agents for the treatment of certain conditions including psoriasis, atherosclerosis and restenosis injuries. Compounds within the scope of the present invention exhibit the modulation and/or inhibition of cell signaling and/or cell proliferation and/or matrix production and/or chemotaxis and/or cell inflammatory response, and can be used in preventing or delaying the occurrence or reoccurrence of such conditions or otherwise treating the condition.

To determine the effectiveness of compounds of this invention, the pharmacological tests described below, which are accepted in the art and recognized to correlate with pharmacological activity in mammals, are utilized. Compounds within the scope of this invention have been subjected to these various tests, and the results obtained are believed to correlate to useful cellular differentiation media-tor activity. The results of these tests are believed to provide sufficient information to persons skilled in the pharmacological and medicinal chemistry arts to determine the parameters for using the studied compounds in one or more of the therapies described herein.

1. PDGF-R Tyrosine Kinase Autophosphorylation ELISA assay

The titled assay is performed as described by Dolle et al. (J. Med. Chem. 1994, 37, 2627), which is incorporated herein by reference, with the exception of using the cell lysates derived from Human aortic smooth muscle cells (HAMSC) as described below.

2. Mitogenesis Assay General Procedure a. Cell Culture

Human aortic smooth muscle cells (passage 4–9) are plated in 96 well plates in a growth supporting medium at 6000 cells/well and allowed to grow 2–3 days. At approximately 85% confluence, cells are growth arrested with serum free media (SFM).

b. Mitogenesis Assay

After 24 hour serum deprivation, medium is removed and replaced with test compound/vehicle in SFM (200 $\mu$l/well). Compounds are solubilized in cell culture DMSO at a concentration of 10 nM and further dilutions are made in SFM.

After 30 min preincubation with compound, cells are stimulated with PDGF at 10 ng/mL. Determinations are performed in duplicate with stimulated and unstimulated wells at each compound concentration.

Four hours later, 1 $\mu$Ci$^3$H thymidine/well is added.

Cultures are terminated 24 hours after addition of growth factor. Cells are lifted with trypsin and harvested onto a filter mat using an automated cell harvester (Wallac MachII96). The filter mat is counted in a scintillation counter (Wallac Betaplate) to determine DNA-incorporated label.

3. Chemotaxis Assay

Human aortic smooth muscle cells (HASMC) at earlier passages are obtained from ATCC. Cells are grown in Clonetics SmGM 2 SingleQuots (media and cells at passages 4–10 are used. When cells are 80% confluent, a fluorescent probe, calcein AM (5 mM, Molecular Probe), is added to the media and cells are incubated for 30 minutes. After washing with HEPES buffered saline, cells are lifted with trypsin and neutralized with MCDB 131 buffer (Gibco) with 0.1% BSA, 10 mM glutamine and 10% fetal bovine serum. After centrifugation, cells are washed one more time and resuspended in the same buffer without fetal bovine serum at 30000 cells/50 mL. Cells are incubated with different concentrations of a compound of formula I (final DMSO concentration= 1%) for 30 min at 37+ C. For chemotaxis studies, 96 well modified Boyden chambers (Neuroprobe, Inc.) and a polycarbonate membrane with 8 mm pore size (Poretics, CA) are used. The membrane is coated with collagen (Sigma C3657, 0.1 mg/mL). PDGF-$\beta\beta$ (3 ng/mL) in buffer with and without a compound of formula I are placed in the lower chamber. Cells (30,000), with and without inhibitor, are placed in the upper chamber. Cells are incubated for 4 hours. The filter membrane is removed and cells on the upper membrane side are removed. After drying, fluoresce on the membrane is determined using Cytofluor II (Millipore) at excitation/emission wavelengths of 485/ 530 nm. In each experiment, an average cell migration is obtained from six replicates. Percent inhibition is determined from DMSO treated control values. From five points concentration-dependent inhibitions, $IC_{50}$ value is calculated. Results are presented as a mean±SEM from five such experiments.

4. EGF-Receptor Purification

EGF-receptor purification is based on the procedure of Yarden and Schlessinger. A431 cells are grown in 80 cm² bottles to confluency ($2 \times 10^7$ cells per bottle). The cells are washed twice with PBS and harvested with PBS containing 11.0 mmol EDTA (1 hour at 37° C., and centrifuged at 600 g for 10 minutes. The cells are solubilized in 1 mL per $2 \times 10^7$ cells of cold solubilization buffer (50 mmol Hepes buffer, pH 7.6, 1% Triton X-100, 150 mmol NaCl, 5 mmol EGTA, 1 mmol PMSF, 50 mg/mL aprotinin, 25 mmol benzamidine, 5 mg/mL leupeptic, and 10 mg/mL soybean trypsin inhibitor) for 20 minutes at 4° C. After centrifugation at 100,000 g for 30 minutes, the supernatant is loaded onto a WGA-agarose column (100 mL of packed resin per $2 \times 10^7$ cells) and shaken for 2 hours at 4° C. The unabsorbed material is removed and the resin washed twice with HTN buffer (50 mmol Hepes, pH 7.6, 0.1% Triton X-100, 150 mmol NaCl), twice with HTN buffer containing 1 M NaCl, and twice with HTNG buffer (50 mmol Hepes, pH 7.6, 0.1% Triton X-100, 150 mmol NaCl, and 10% glycerol). The EGF receptor is eluted batchwise with HTNG buffer containing 0.5 N-acetyl-D-glucosamine (200 mL per $2 \times 10^7$ cells.). The eluted material is stored in aliquots at −70° C. and diluted before use with TMTNG buffer (50 mmol Tris-Mes buffer, pH 7.6, 0.1% Triton X-100, 150 mmol NaCl, 10% glycerol).

5. Inhibition of EGF-R Autophosphorylation

A431 cells are grown to confluence on human fibronectin coated tissue culture dishes. After washing 2 times with ice-cold PBS, cells are lysed by the addition of 500 mL/dish of lysis buffer (50 mmol Hepes, pH 7.5, 150 mmol NaCl, 1.5 mmol $MgCl_2$, 1 mmol EGTA, 10% glycerol, 1% triton X-100, 1 mmol PMSF, 1 mg/mL aprotinin, 1 mg/mL leupeptin) and incubating 5 minutes at 4° C. After EGF stimulation (500 mg/mL 10 minutes at 37° C.) immunoprecipitation is performed with anti EGF-R (Ab 108) and the autophosphorylation reaction (50 mL aliquots, 3 mCi [g-$^{32}$P]ATP) sample is carried out in the presence of 2 or 10 mM of compound of the present invention, for 2 minutes at 4° C. The reaction is stopped by adding hot electrophoresis sample buffer. SDA-PAGE analysis (7.5% els) is followed by autoradiography and the reaction is quantitated by densitometry scanning of the x-ray films.

a. Cell Culture

Cells termed HER 14 and K721A are prepared by transfecting NIH3T3 cells (clone 2.2) (From C. Fryling, NCI, NIH), which lack endogenous EGF-receptors, with cDNA constructs of wild-type EGF-receptor or mutant EGF-receptor lacking tyrosine kinase activity (in which Lys 721 at the ATP-binding site is replace by an Ala residue, respectively). All cells are grown in DMEM with 10% calf serum (Hyclone, Logan, Utah).

6. Selectivity vs. PKA and PKC is determined using commercial kits:

a. Pierce Colorimetric PKA Assay Kit, Spinzyme Format Brief Protocol:
   PKA enzyme (bovine heart) IU/assay tube
   Kemptide peptide (dye labeled) substrate
   45 minutes @ 30° C.
   Absorbance at 570 nm b. Pierce Colorimetric PKC Assay kit, Spinzyme Format Brief Protocol:
   PKC enzyme (rat brain) 0.025 U/assay tube
   Neurogranin peptide (dye labeled) substrate
   30 minutes @ 30° C.
   Absorbance at 570 nm 7. $p56^{lck}$ Tyrosine Kinase Inhibition Activity Measurements $p56^{lck}$ Tyrosine kinase inhibition activity is determined according to a procedure disclosed in U.S. Pat. No. 5,714,493, incorporated herein by reference.

In the alternative, the tyrosine kinase inhibition activity is determined according to the following method. A substrate (tyrosine-containing substrate, Biot-(β Ala)$_3$-Lys-Val-Glu-Lys-Ile-Gly-Glu-Gly-Thr-Tyr-Glu-Val-Val-Tyr-Lys-(NH$_2$) recognized by P56$^{lck}$, 1 μM) is first phosphorylated in presence or absence of a given concentration of the test compound, by a given amount of enzyme (enzyme is produced by expression of P56$^{lck}$ gene in a yeast construct) purified from a cloned yeast (purification of the enzyme is done by following classical methods) in the presence of ATP (10 μM) MgCl2 (2.5 mM), MnCl2 (2.5 mM), NaCl (25 mM), DTT (0.4 mM) in Hepes 50 mM, pH 7.5, over 10 min at ambient temperature. The total reaction volume is 50 μl, and the reactions are performed in a black 96-well fluoroplate. The reaction is stopped by addition of 150 μl of stopping buffer (100 mM Hepes pH 7.5, KF 400 mM, EDTA 133 mM, BSA lg/l.) containing a selected anti tyrosine antibody labelled with the Europium cryptate (PY20-K) at 0.8 μg/ml and allophycocyanine-labelled streptavidin (XL665) at 4 μg/ml. The labelling of Streptavidin and anti-tyrosine antibodies were performed by Cis-Bio International (France). The mixture is counted using a Packard Discovery counter which is able to measure time-resolved homogeneous fluorescence transfer (excitation at 337 nm, readout at 620 nm and 665 nm). The ratio of the 665 nm signal/620 nm signal is a measure of the phosphorylated tyrosine concentration. The blank is obtained by replacing enzyme by buffer. The specific signal is the difference between the ratio obtained without inhibitor and the ratio with the blank. The percentage of specific signal is calculated. The $IC_{50}$ is calculated with 10 concentrations of inhibitor in duplicate using Xlfit soft. The reference compound is staurosporine (Sigma) and it exhibits an $IC_{50}$ of 30±6 nM (n=20).

8. Measurement of Tumor Inhibition In Vitro

The inhibition of tumor growth in vitro by the compounds of this invention is determined as follows:

C6 rat glioma cell line (provided by ATCC) is grown as monolayers in Dubelcco's Modified Eagle Medium containing 2 mM L-glutamine, 200 U/ml penicillin, 200 μg/ml streptomycin and supplemented with 10% (v/v) heat inactivated foetal calf serum. Cells in exponential phase of growth are trypsinized, washed with PBS and diluted to a final concentration of 6500 cells/ml in complete medium. Drug to be tested or control solvent are added to the cell suspension (2.5 ml under a volume of 50 μl and 0.4 ml of 2.4% Noble Difco agar maintained at 45° C. are added and mixed. The mixture is immediately poured into Petri dishes and left standing for 5 minutes at 4° C. The number of cellular clones (>60 cells) are measured after 12 days of incubation at 37° C. under 5% $CO_2$ atmosphere. Each drug is tested at 10, 1, 0.1, and 0.01 μg/ml (final concentration in the agar) in duplicate. Results are expressed in percent inhibition of clonogenicity relatively to untreated controls. $IC_{50}$'s are determined graphically from semi-logarithmic plots of the mean value determined for each drug concentration.

9. Measurement of Tumor Inhibition In Vivo

The inhibition of tumor growth in vivo by the compounds of this invention is determined using a subcutaneous xenograft model as described in U.S. Pat. Nos. 5,700,823 and 5,760,066, in which mice are implanted with C6 glioma cells and tumor growth is measured using venier calipers.

The results obtained by the above experimental methods evidence that the compounds within the scope of the present invention possess useful PDGF receptor protein tyrosine kinase inhibition properties or $p56^{lck}$ tyrosine kinase inhibition properties, and thus possess therapeutic value. The above pharmacological test results may be used to determine the dosage and mode of administration for the particular therapy sought.

The present invention may be embodied in other specific forms without departing from the spirit or essential attributes thereof.

We claim:

1. A compound of formula I

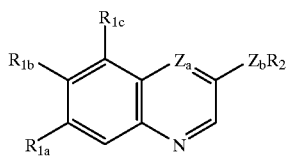

(I)

wherein $R_{1a}$ is optionally substituted one to ten carbon atom alkyl, hydroxy, acyloxy, optionally substituted one to ten carbon atom alkoxy, optionally substituted three to seven carbon atom cyclo-alkyloxy, optionally substituted four to seven ring member oxaheterocyclyloxy, optionally substituted four to seven ring member heterocyclylcarbonyloxy or halo;

$R_{1b}$ is hydrogen, optionally substituted one to ten carbon atom alkyl, hydroxy, acyloxy, optionally sutstituted one to ten carbon atom alkoxy, optionally substituted three to seven carbon atom cycloalkyloxy, optionally substituted four to seven ring member oxaheterocyclyloxy, optionally substituted four to seven ring member heterocyclylcarbonyloxy or halo;

$R_{1c}$ is hydrogen, optionally substituted one to ten carbon atom alkyl, optionally substituted phenyl or naphthyl, optionally substituted five to ten ring member heteroaryl, hydroxy, acyl-oxy, optionally substituted one to ten carbon atom alkoxy, optionally substituted three to seven carbon atom cycloalkyloxy, optionally substituted four to seven ring member heterocyclyloxy, optionally substituted phenyloxy or naphthyloxy, optionally substituted five to ten ring member heteroaryloxy, optionally substituted four to seven ring member heterocyclylcarbonyloxy, halo, cyano, $R_5R_6N$- or acyl$R_5N$-;

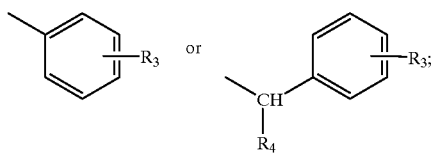

$R_3$ is hydrogen, or ortho or para fluoro, or meta lower alkyl, lower akloxy, fluoro, bromo, iodo or carbamoyl;

$R_4$ is hydrogen or lower alkyl;

$R_5$ and $R_6$ are independently hydrogen or alkyl, or $R_5$ or $R_6$ taken together with the nitrogen atom to which $R_5$ and $R_6$ are attached form a four to seven ring member azaheterocyclyl;

$Z_a$ is N; and $Z_b$ is NH or O, or an N-oxide thereof, hydrate thereof, solvate thereof, prodrug thereof, or salt thereof, provided that $R_{1a}$ and $R_{1b}$ are not both optionally substituted alkyl.

2. The compound of claim 1 wherein $R_{1a}$ is optionally substituted lower alkoxy, optionally substituted mono cyclic cycloalkyloxy, optionally substituted heterocyclylcarbonyloxy or optionally substituted mono cyclic oxoheterocyclyloxy.

3. The compound of claim 2 wherein $R_{1a}$ is optionally substituted lower alkoxy or optionally substituted mono cyclic oxaheterocyclyloxy.

4. The compound of claim 3 wherein $R_{1a}$ is methoxy, ethoxy, 2-(ethoxy)ethoxy, 2-(4-morpholinyl)ethoxy or furanyloxy.

5. The compound of claim 1 wherein $R_{1b}$ is hydrogen, optionally substituted lower alkoxy, optionally substituted mono cyclic cycloalkyloxy, optionally substituted heterocyclylcarbonyloxy or optionally substituted mono cyclic oxaheterocyclyloxy.

6. The compound of claim 5 wherein $R_{1b}$ is hydrogen or optionally substituted lower alkoxy.

7. The compound of claim 6 wherein $R_{1b}$ is methoxy or ethoxy.

8. The compound of claim 1 wherein $R_{1a}$ and $R_{1b}$ are lower alkoxy.

9. The compound of claim 8 wherein $R_{1a}$ and $R_{1b}$ are methoxy or ethoxy.

10. The compound of claim 1 wherein $R_{1c}$ is hydrogen or optionally substituted lower alkoxy.

11. The compound of claim 10 wherein $R_{1c}$ is hydrogen, methoxy or ethoxy.

12. The compound of claim 1 wherein $R_2$ is

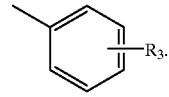

13. The compound of claim 1 wherein $R_2$ is

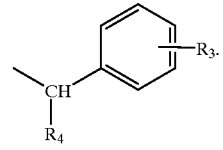

14. The compound of claim 1 wherein $R_3$ is hydrogen, ortho or para s fluoro, or meta methyl, trifluoromethyl, methoxy, fluoro, chloro, bromo or carbamoyl.

15. The compound of claim 1 wherein $R_4$ is hydrogen or methyl.

16. The compound of claim 1 wherein $Z_b$ is NH.

17. The compound of claim 1 wherein $Z_b$ is O.

18. A compound of claim 1 which is selected from the following species:

2-anilino-6-quinoxalinol;

2-((R)-α-Methylbenzyl-amino)-6,7-diethoxyquinoxaline;

2-anilino-6-isopropoxyquinoxaline;
2-Phenoxy-6-methoxyquinoxaline;
(3-Bromobenzyl)-(6,7-dimethoxyquinoxalin2-yl)-amine;
2-(3-Carbamoylphenylamino)-6-methoxyquinoxaline;
2-(2-Fluorophenylamino)-6,7-diethoxyquinoxaline;
2-(3-Trifluoromethylphenylamino)-6,7-diethoxyquinoxaline;
Phenyl-[6-(tetrahydrofuran-3(R)-yloxy)quinoxalin-2-yl]amine;
Benzyl-(6,7-dimethoxyquinoxalin-2-yl)-amine;
2-((S)-α-Methylbenzyl-amino)-6,7-diethoxyquinoxaline;
2-Benzylamino-6,7-diethoxyquinoxaline;
(6-Methoxyquinoxalin-2-yl)-(3-methylphenyl)-amine;
6-Methoxy-2-phenylamino-quinoxaline;
2-Anilino-6-ethoxyquinoxaline;
2-(3-Methoxyphenylamino)-6,7-diethoxyquinoxaline;
2-(4-Fluorophenylamino)-6,7-diethoxyquinoxaline;
6,7-Diethoxy-2-phenoxyquinoxaline;
2-Phenylamino-6,7-diethoxyquinoxaline;
(6,7-Dimethoxyquinoxalin-2-yl)-(3-fluorophenyl)-amine;
2-(3-Fluorophenylamino)-6,7-diethoxyquinoxaline;
(3-Bromophenyl)-(6,7-dimethoxyquinoxalin-2-yl)-amine;
(6,7-Dimethoxyquinoxalin-2-yl)-phenyl-amine; and
(3-Chlorophenyl)-(6,7-dimethoxyquinoxalin-2-yl)-amine, or
an N-oxide thereof, hydrate thereof, solvate thereof, prodrug thereof, or pharmaceutically acceptable salt thereof.

19. A compound of claim 1 which is selected from the species:
Phenyl-[6-(tetrahydrofuran-3(R)-yloxy)quinoxalin-2-yl]amine;
Benzyl-(6,7-dimethoxyquinoxalin-2-yl)-amine;
2-((S)-α-Methylbenzyl-amino)-6,7-diethoxyquinoxaline;
2-Benzylamino-6,7-diethoxyquinoxaline;
(6-Methoxyquinoxalin-2-yl)-(3-methylphenyl)-amine;
6-Methoxy-2-phenylamino-quinoxaline;
2-Anilino-6-ethoxyquinoxaline;
2-(3-Methoxyphenylamino)-6,7-diethoxyquinoxaline;
2-(4-Fluorophenylamino)-6,7-diethoxyquinoxaline;
6,7-Diethoxy-2-phenoxyquinoxaline;
2-Phenylamino-6,7-diethoxyquinoxaline;
(6,7-Dimethoxyquinoxalin-2-yl)-(3-fluorophenyl)-amine;
2-(3-Fluorophenylamino)-6,7-diethoxyquinoxaline;
(3-Bromophenyl)-6,7-dimethoxyquinoxalin-2-yl)-amine;
(6,7-Dimethoxyquinoxalin-2-yl)-phenyl-amine; and
(3-Chlorophenyl)-(6,7-dimethoxyquinoxalin-2-yl)-amine, or
an N-oxide thereof, hydrate thereof, solvate thereof, prodrug thereof, or pharmaceutically acceptable salt thereof.

20. The compound according to claim 1 which is Phenyl-[6-(tetrahydrofuran-3(R)-yloxy)quinoxalin-2-yl]amine, or an N-oxide thereof, hydrate thereof, solvate thereof, prodrug thereof, or pharmaceutically acceptable salt thereof.

21. The compound according to claim 1 which is Benzyl-(6,7-dimethoxyquinoxalin-2-yl)-amine, or an N-oxide thereof, hydrate thereof, solvate thereof, prodrug thereof, or pharmaceutically acceptable salt thereof.

22. The compound according to claim 1 which is 2-((S)-α-Methylbenzyl-amino)-6,7-diethoxyquinoxaline, or an N-oxide thereof, hydrate thereof, solvate thereof, prodrug thereof, or pharmaceutically acceptable salt thereof.

23. The compound according to claim 1 which is 2-Benzylamino-6,7-diethoxyquinoxaline, or an N-oxide thereof, hydrate thereof, solvate thereof, prodrug thereof, or pharmaceutically acceptable salt thereof.

24. The compound according to claim 1 which is (6-Methoxyquinoxalin-2-yl)-(3-methylphenyl)-amine, or an N-oxide thereof, hydrate thereof, solvate thereof, prodrug thereof, or pharmaceutically acceptable salt thereof.

25. The compound according to claim 1 which is 6-Methoxy-2-phenylamino-quinoxaline, or an N-oxide thereof, hydrate thereof, solvate thereof, prodrug thereof, or pharmaceutically acceptable salt thereof.

26. The compound according to claim 1 which is 2-Anilino-6-ethoxyquinoxaline, or an N-oxide thereof, hydrate thereof, solvate thereof, prodrug thereof, or pharmaceutically acceptable salt thereof.

27. The compound according to claim 1 which is 2-(3-Methoxyphenylamino-6,7-diethoxyquinoxaline, or an N-oxide thereof, hydrate thereof, solvate thereof, prodrug thereof, or pharmaceutically acceptable salt thereof.

28. The compound according to claim 1 which is 2-(4-Fluorophenylamino)-(6,7-diethoxyquinoxaline, or an N-oxide thereof, hydrate thereof, solvate thereof, prodrug thereof, or pharmaceutically acceptable salt thereof.

29. The compound according to claim 1 which is 6,7-Diethoxy-2-phenoxyquinoxaline, or an N-oxide thereof, hydrate thereof, solvate thereof, prodrug thereof, or pharmaceutically acceptable salt thereof.

30. The compound according to claim 1 which is 2-Phenylamino-6,7-diethoxyquinoxaline, or an N-oxide thereof, hydrate thereof, solvate thereof, prodrug thereof, or pharmaceutically acceptable salt thereof.

31. The compound according to claim 1 which is (6,7-Dimethoxyquinoxalin-2-yl)-(3-fluorophenyl)-amine, or an N-oxide thereof, hydrate thereof, solvate thereof, prodrug thereof, or pharmaceutically acceptable salt thereof.

32. The compound according to claim 1 which is 2-(3-Fluorophenylamino)-6,7-diethoxyquinoxaline, or an N-oxide thereof, hydrate thereof, solvate thereof, prodrug thereof, or pharmaceutically acceptable salt thereof.

33. The compound according to claim 1 which is (3-Bromophenyl)-(6,7-dimethoxyquinoxalin-2-yl)-amine, or an N-oxide thereof, hydrate thereof, solvate thereof, prodrug thereof, or pharmaceutically acceptable salt thereof.

34. The compound according to claim 1 which is (6,7-Dimethoxyquinoxalin-2-yl)-phenyl-amine, or an N-oxide thereof, hydrate thereof, solvate thereof, prodrug thereof, or pharmaceutically acceptable salt thereof.

35. The compound according to claim 1 which is (3-Chlorophenyl)-(6,7-dimethoxyquinoxalin-2yl)-amine, or an N-oxide thereof, hydrate thereof, solvate thereof, prodrug thereof, or pharmaceutically acceptable salt thereof.

36. A pharmaceutically composition comprising the compound of claim 1 and a pharmaceutically acceptable carrier.

* * * * *